United States Patent [19]
Tsusaki et al.

[11] Patent Number: 6,087,146
[45] Date of Patent: *Jul. 11, 2000

[54] RECOMBINANT THERMOSTABLE ENZYME FOR CONVERTING MALTOSE INTO TREHALOSE

[75] Inventors: Keiji Tsusaki; Michio Kubota, both of Okayama, Japan

[73] Assignee: Kabushiki Kaisha Hayashibara Seibutsu Kagaku Kenkyujo, Okayama, Japan

[ * ] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/863,010

[22] Filed: May 23, 1997

Related U.S. Application Data

[63] Continuation of application No. 08/537,002, Sep. 29, 1995, Pat. No. 5,773,282.

[30] Foreign Application Priority Data

| Oct. 1, 1994 | [JP] | Japan | 6-260984 |
| Sep. 8, 1995 | [JP] | Japan | 7-255829 |

[51] Int. Cl.[7] .............. C12N 9/24; C12N 1/20; C12P 19/12; C07H 21/04
[52] U.S. Cl. ............ 435/200; 435/100; 435/252.3; 435/440; 536/23.2; 536/24.3
[58] Field of Search .................... 435/100, 200, 435/252.3, 440; 536/23.2, 24.3

[56] References Cited

U.S. PATENT DOCUMENTS

| Re. 33,047 | 9/1989 | Miyake et al. | 127/46.3 |
| 4,521,252 | 6/1985 | Miyake et al. | 127/46.3 |
| 5,538,883 | 7/1996 | Nishimoto et al. | 435/200 |

FOREIGN PATENT DOCUMENTS

| 0636693 | 2/1995 | European Pat. Off. . |
| 0693558 | 1/1996 | European Pat. Off. . |
| 50-154485 | 12/1975 | Japan . |
| 58-23799 | 2/1983 | Japan . |
| 58-72598 | 4/1983 | Japan . |
| 58-216695 | 12/1983 | Japan . |

OTHER PUBLICATIONS

Gherna, et al (eds.), ATCC *Catalogue of Bacteria and Phages*, 18th Ed. (1992), pp. 366–367.

Laemmli, U.K., "Cleavage of Structural Proteins during the Assembly of the Head of Bacteriophage T4"; *Nature*, 227:680–685 (1970).

Nishimoto, et al, "Existence of a Novel Enzyme Converting Maltose into Trehalose"; *Biosci, Biotech, Biochem*, 59(11):2189–2190 (1995).

Nishimoto, et al, "Purification and Properties of a Novel Enzyme, Trehalose Synthase, from Primelobacter sp. R48"; *Biosci, Biotech, Biochem*, 60(4):640–644 (1996).

Nishimoto, et al, "Purification and Characterization of a Thermostable Trehalose Synthase from Thermus aquaticus"; *Biosci. Biochem. Biotech.*, 60(5):835–839 (1996).

Sambrook, et al, *Molecular Cloning A Laboratory Manual*, 2nd Ed., Cold Spring Harbor Laboratory Press (Plainview, NY 1989); pp. xi=xxxviii.

Sambrook, et al, *Molecular Cloning A Laboratory Manual*, 2nd Ed., Cold Spring Harbor Laboratory Press (Plainview, NY 1989); pp. 1.74–1.81.

Sambrook, et al. Molecular Cloning A Laboratory Manual, 2nd Ed., Cold Spring Harbor Laboratory Press (plainview, NY 1989); pp. 11.3–11.19.

Southern, E.M., "Detection of Specific Sequences Among DNA Fragments Separated by Gel Electrophoresis"; *J. Mol. Biol.*, 98:503–517 (1975).

Tsusaki, et al, "Cloning and sequencing of trehalose synthase gene from Primelobacter sp. R48"; *Biochimica et Biophysica Acta*, 1290:1–3 (1996).

*Primary Examiner*—Lisa J. Hobbs
*Attorney, Agent, or Firm*—Browdy and Neimark

[57] ABSTRACT

Disclosed are a recombinant thermostable enzyme, which converts maltose into trehalose and is stable up to a temperature of about 80° C. even when incubated at pH 7.0 for 60 min, a preparation of the enzyme, a DNA encoding the enzyme, a recombinant DNA containing the DNA, a transformant, and an enzymatic conversion method of maltose by using the enzyme.

5 Claims, 6 Drawing Sheets

— ● — Acetate buffer
— ○ — Phosphate buffer
— ◐ — Sodium carbonate/sodium hydrogen carbonate buffer

RECOMBINANT THERMOSTABLE ENZYME FOR CONVERTING MALTOSE INTO TREHALOSE

This application is a continuation of Ser. No. 08/537,002 filed Sep. 29, 1995 now U.S. Pat. No. 5,773,282.

BACKGROUND OF THE INVENTION

1. Field of the Invention

The present invention relates to a novel recombinant thermostable enzyme which converts maltose into trehalose.

1. Description of the Prior Art

Trehalose is a disaccharide which consists of 2 glucose molecules linked together with their reducing groups, and, naturally, it is present in bacteria, fungi, algae, insects, etc., in an extremely-small quantity. Having no reducing residue within the molecule, trehalose does not cause an unsatisfactory browning reaction even when heated in the presence of amino acids or the like, and because of this it can advantageously sweeten food products without fear of causing unsatisfactory coloration and deterioration. However, trehalose is far from being readily prepared in a desired amount by conventional methods, and, actually, it is not scarcely used for sweetening food products.

Conventional methods are roughly classified into 2 groups, i.e. the one using cells of microorganisms and the other employing a multi-enzymatic system wherein enzymes are allowed to act on saccharides. The former, as disclosed in Japanese Patent Laid-Open No.154,485/75, is a method which comprises allowing to grow microorganisms such as bacteria and yeasts in a nutrient culture medium, and collecting trehalose from the resultant culture. The latter, as disclosed in Japanese Patent Laid-Open No.216,695/83, is a method which comprises providing maltose as a substrate, allowing a multi-enzymatic system using maltose- and trehalose-phosphorylases to act on maltose, and isolating the formed trehalose from the reaction system. Although the former facilitates the growth of microorganisms without special difficulty, it has a drawback that the resultant culture only contains at most 15 w/w % trehalose, on a dry solid basis (d.s.b.). While the latter enables the separation of trehalose with a relative easiness, but it is theoretically difficult to increase the trehalose yield by allowing enzymes to act on substrates at a considerably-high concentration because the enzymatic reaction per se is an equilibrium reaction of 2 different types of enzymes and the equilibrium point constantly inclines to the side of forming glucose phosphate.

In view of the foregoing, the present inventors energetically screened enzymes which directly convert maltose into trehalose, and have found that microorganisms belonging to those of the genera Pimelobacter and Pseudomonas, as disclosed in Japanese Patent Application No.199,971/93, produce an absolutely novel enzyme which forms trehalose when acts on maltose. This means that trehalose can be prepared from maltose as a material which is readily available in quantity and at low cost, and the use of the enzyme would completely overcome all the aforesaid objects.

It was found that all the enzymes from these microorganisms have an optimum temperature of about 20–40° C. which seems some how insufficient for trehalose production in their thermostability. It is recognized in this field that the saccharification of starch and amylaceous substances should be generally reacted at a temperature of over 55° C.: If the saccharification reaction is effected at a temperature of 55° C. or lower,, bacterial contamination is enhanced to lower the pH of the reaction mixtures and to inactivate enzymes used, followed by remaining a relatively large amount of substrates intact. If the saccharification reaction is effected by using enzymes with poor thermostability, a great care should be taken for the pH changes, and, once a pH lowering occurs, alkalis should be quickly added to the reaction mixtures to increase the pH.

In view of the foregoing, the present inventors further studied on thermostable enzymes with such activity and have found that enzymes, produced from microorganisms of the genus Thermus such as a microorganism of the species *Thermus aquaticus* (ATCC 33923), effectively convert maltose into trehalose without being substantially inactivated even when reacted at a temperature of over 55° C. These enzymes, however, are not sufficient in enzyme producing activity, and this leads to a problem of that an industrial scale production of trehalose inevitably requires a considerably large scale cultivation of such microorganisms.

Recombinant DNA technology has made a remarkable progress in recent years. At present, even an enzyme, whose total amino acid sequence is not revealed, can be readily prepared in a desired amount, if a gene encoding the enzyme was once isolated and the base sequence was decoded, by preparing a recombinant DNA containing a DNA which encodes the enzyme, introducing the recombinant DNA into microorganisms or cells of plants or animals, and culturing the resultant transformants. Under these circumstances, urgently required are to find a gene encoding the above thermostable enzyme and to decode the base sequence.

SUMMARY OF THE INVENTION

It is an object of the present invention to provide a recombinant thermostable enzyme which forms trehalose when acts on maltose.

It is a further object of the present invention to provide a DNA which encodes the recombinant enzyme.

It is yet another object of the present invention to provide a replicable recombinant DNA having the DNA.

It is a further object of the present invention to provide a transformant into which the recombinant DNA has been introduced.

It is a further object of the present invention to provide a process for preparing the recombinant enzyme by using the transformant.

It is a further object of the present invention to provide a method for converting maltose into trehalose by the recombinant enzyme.

[Means to Attain the Object]

The first object of the present invention is attained by a recombinant enzyme.

The second object of the present invention is attained by a DNA which encodes the recombinant enzyme.

The third object of the present invention is attained by a replicable recombinant DNA which contains the DNA and a self-replicable vector.

The fourth object of the present invention is attained by a transformant obtained by introducing the replicable recombinant DNA into an appropriate host.

The fifth object of the present invention is attained by culturing the transformant in a nutrient culture medium to form the recombinant enzyme, and collecting the formed recombinant enzyme from the resultant culture.

The sixth object of the present invention is attained by an enzymatic conversion method of maltose which contains a step of allowing the recombinant enzyme to act on maltose to form trehalose.

BRIEF DESCRIPTION OF THE ACCOMPANYING DRAWINGS

DETAILED DESCRIPTION OF THE INVENTION

Figure 1:
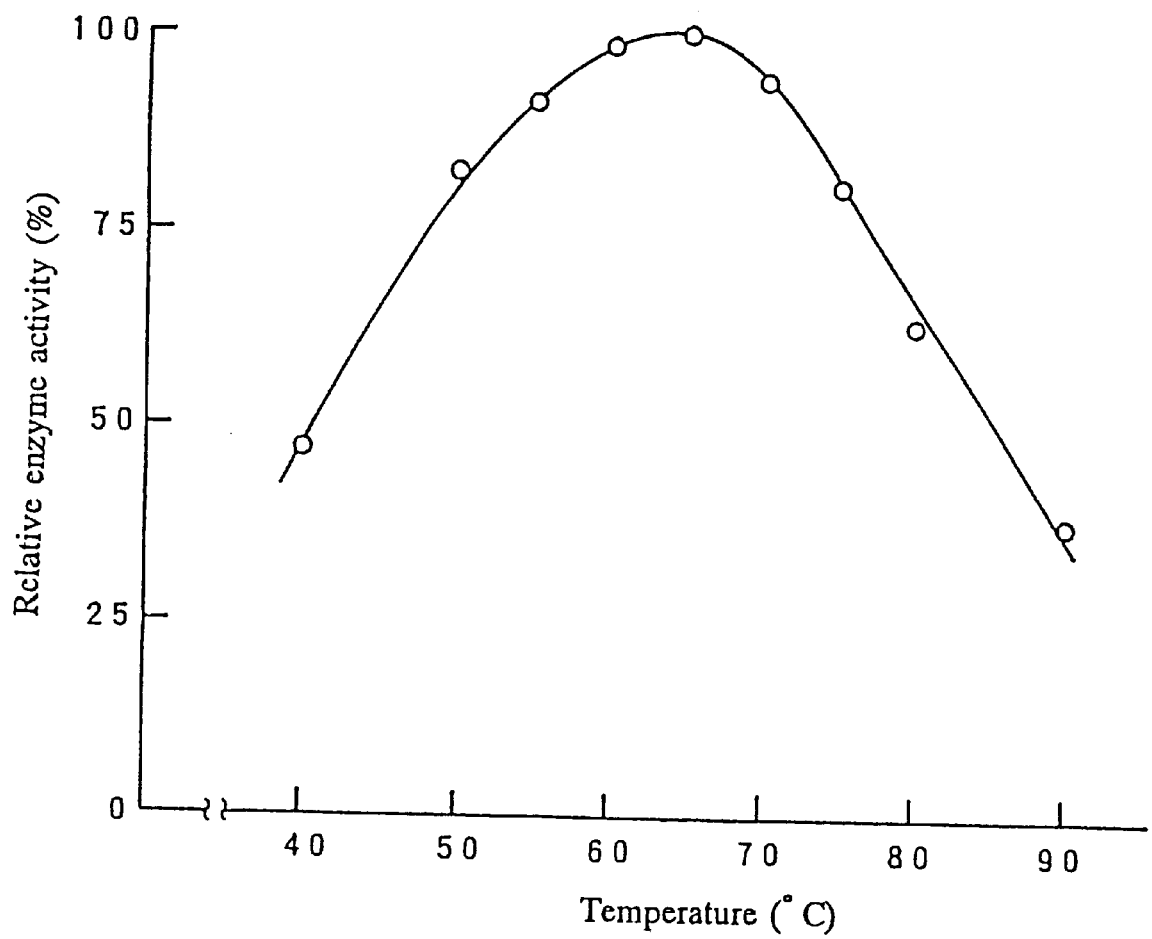
FIG. 1 shows the optimum temperature of an enzyme produced from *Thermus aquaticus* (ATCC 33923).

The recombinant enzyme according to the present invention acts on maltose to form trehalose without being substantially inactivated even when allowed to react at a temperature of over 55° C.

The DNA according to the present invention expresses the production of the present recombinant enzyme when introduced into an appropriate self-replicable vector to obtain a replicable recombinant DNA, then introduced into an appropriate host, which is inherently incapable of forming the recombinant enzyme but readily proliferative, to form a transformant.

The recombinant DNA according to the present invention expresses the production of the recombinant enzyme by introducing it into an appropriate host, which is inherently incapable of forming the recombinant enzyme but readily proliferative, to form a transformant, and culturing the transformant in a nutrient culture medium.

The transformant forms a desired amount of the recombinant enzyme when cultured according to the present invention.

The enzymatic conversion method according to the present invention converts maltose into a saccharide composition comprising trehalose, glucose and/or maltooligosaccharides.

The present invention was made based on the finding of an absolutely novel thermostable enzyme which converts maltose into trehalose. Such an enzyme can be obtained from cultures of *Thermus aquaticus* (ATCC 33923), and the present inventors isolated the enzyme by using a variety of methods comprising column chromatography as a main technique, and studied on the properties and features, revealing that the reality is a polypeptide having the following physicochemical properties:

| | | |
|---|---|---|
| (1) | Action | Forming trehalose when acts on maltose, and vice versa; |
| (2) | Molecular weight (MW) | About 100,000–110,000 daltons when assayed on sodium dodecyl sulfate polyacrylamide gel electrophoresis (SDS-PAGE); |
| (3) | Isoelectric point (pI) | About 3.8–4.8 when assayed on isoelectrophoresis; |
| (4) | Optimum temperature | About 65° C. when incubated at pH 7.0 for 60 min; |
| (5) | Optimum pH | About 6.0–6.7 when incubated at 60° C. for 60 min; |
| (6) | Thermal stability | Stable up to a temperature of about 80° C. even when incubated at pH 7.0 for 60 min; and |
| (7) | pH Stability | Stable up to a pH of 5.5–9.5 even when incubated at 60° C. for 60 min. |

Experiments for revealing the physicochemical properties of a thermostable enzyme produced from *Thermus aquaticus* (ATCC 33923) are as follows:

EXPERIMENT 1

Purification of Enzyme

Experiment 1-1

Production of Enzyme

In 500-ml Erlenmeyer flasks were placed 100 ml aliquots of a liquid culture medium (pH 7.5) containing 0.5 w/v % polypeptone, 0.1 w/v % yeast extract, 0.07 w/v % sodium nitrate, 0.01 w/v % disodium hydrogen phosphate, 0.02 w/v % magnesium sulfate heptahydrate, 0.01 w/v % calcium chloride, and water, and the flasks were autoclaved at 120° C. for 20 min to effect sterilization. After cooling the flasks a seed culture of *Thermus aquaticus* (ATCC 33923) was inoculated into each flask, followed by the incubation at 60° C. for 24 hours under a rotary-shaking condition of 200 rpm to obtain a seed culture. Twenty L aliquots of a fresh preparation of the same liquid culture medium were put in 30-L jar fermenters, sterilized and cooled to 60° C., followed by inoculating one v/v % of the seed culture into each fermenter, and incubating the resultant at a pH of 6.0–8.0 and 60° C. for about 20 hours under aeration-agitation conditions.

Thereafter, the enzymatic activity of the resultant culture was assayed to reveal that it contained about 0.35 units/ml of the enzyme. A portion of the culture was centrifuged, and the supernatant was assayed to reveal that it contained about 0.02 units/ml of the enzyme. While the separated cells were suspended in 50 mM phosphate buffer (pH 7.0) to give the total volume equal to the original volume of the portion, followed by assaying the suspension to reveal that it contained about 0.33 units/ml of the enzyme.

Throughout the specification the enzyme activity is expressed by the value measured on the following assay: Place one ml of 10 mM phosphate buffer (pH 7.0) containing 20 w/v % maltose in a test tube, add one ml of an appropriately diluted enzyme solution to the tube, and incubate the solution in the tube at 60° C. for 60 min to effect an enzymatic reaction, followed by a further incubation at 100° C. for 10 min to suspend the enzymatic reaction. Thereafter, a portion of the reaction mixture was diluted by 11 times with 50 mM phosphate buffer (pH 7.5), and 0.4 ml of which was placed in a test tube, admixed with 0.1 ml solution containing one unit/ml trehalase, followed by incubating the resultant mixture at 45° C. for 120 min and quantifying the glucose content on the glucose oxidase method. As a control, a system using a trehalase solution and an enzyme solution which has been inactivated by heating at 100° C. for 10 min is provided and treated similarly as above. The content of the formed trehalose is estimable based on the content of glucose quantified in the above. One unit of the enzyme activity is defined as the amount which forms one $\mu$mol trehalose per min under the above conditions.

Experiment 1-2

Purification of Enzyme

The culture obtained in Experiment 1-1 was centrifuged to separate cells, and about 0.28 kg of the wet cells thus obtained was suspended in 10 mM phosphate buffer (pH 7.0), disrupted in usual manner, and centrifuged to obtain an about 1.8 L of a crude enzyme solution. The solution was admixed with ammonium sulfate to give a saturation of 70 w/v %, salted out by standing at 4° C. overnight, and centrifuged to obtain a supernatant. The supernatant was mixed with 10 mM phosphate buffer (pH 7.0), and the mixture solution was dialyzed against a fresh preparation of the same buffer for 24 hours.

The dialyzed inner solution was centrifuged to obtain a supernatant (1,560 ml) which was then applied to a column packed with 530 ml of "DEAE-TOYOPEARL® 650", an ion exchanger commercialized by Tosoh Corporation, Tokyo, Japan, which had been previously equilibrated with 10 mM phosphate buffer (pH 7.0), followed by feeding to the column a linear gradient buffer of sodium chloride ranging from 0 M to 0.4 M in 10 mM phosphate buffer (pH 7.0). From the eluate, fractions with the objective enzyme activity were collected, pooled, dialyzed against 10 mM phosphate buffer (pH 7.0) containing one M ammonium sulfate for 10 hours, and centrifuged to obtain a supernatant. The supernatant was applied to a column packed with 380 ml of "BUTYL-TOYOPEARL® 650", a gel for hydrophobic chromatography commercialized by Tosoh Corporation, Tokyo, Japan, which had been previously equilibrated with 10 mM phosphate buffer (pH 7.0) containing one M ammonium sulfate, followed by feeding to the column a linear gradient buffer of ammonium sulfate ranging from 1 M to 0 M in 10 mM phosphate buffer (pH 7.0).

Fractions, eluted at 0.2 M ammonium sulfate, with the objective enzyme activity were collected, pooled and dialyzed against 10 mM phosphate buffer (pH 7.0) containing 0.2 M sodium chloride for 16 hours. The dialyzed solution was centrifuged to remove insoluble substances, fed to a column packed with 380 ml of "TOYOPEARL® HW-55S", a gel for gel filtration chromatography commercialized by Tosoh, Corporation, Tokyo, Japan, which had been previously equilibrated with 10 mM phosphate buffer (pH 7.0) containing 0.2 M sodium chloride, followed by feeding to the column with 10 mM phosphate buffer (pH 7.0) containing one M sodium chloride. Fractions with the enzyme activity were collected from the eluate, fed to a column packed with "MONO Q HR5/5" which had been equilibrated with 10 mM phosphate buffer (pH 7.0). The column was fed with a linear gradient buffer of sodium chloride ranging from 0.1 M to 0.35 M in 10 mM phosphate buffer (pH 7.0), followed by collecting fractions with the enzyme activity. The purified enzyme thus obtained had a specific activity of about 135 units/mg protein in a yield of about 330 units per L of the culture.

The purified enzyme was electrophoresed in a 7.5 w/v % polyacrylamide gel to give a single protein band with the enzyme activity, and this meant that it had a considerably-high purity.

EXPERIMENT 2

Physicochemical Property of Enzyme

Experiment 2-1

Action

To an aqueous solution containing 5 w/w % maltose or trehalose as a substrate was added 2 units/g substrate of the purified enzyme obtained in Experiment 1-2, and the mixture was incubated at 60° C. and pH 7.0 for 24 hours. In order to analyze the saccharide composition of the reaction mixture, it was dried in vacuo, dissolved in pyridine, and trimethylsilylated in usual manner, and the resultant was subjected to gas chromatography. The equipments and conditions used in this analysis were as follows: "GC-16A" commercialized by Shimadzu Seisakusho, Ltd., Tokyo, Japan, as a gas chromatograph; a stainless steel column, having an inner diameter of 3 mm and a length of 2 m, packed with 2% "SILICONE OV-17/CHROMOSOLB W" commercialized by GL Sciences Inc., Tokyo, Japan, as a column; a hydrogen flame type of ionization as a detector; nitrogen gas as a carrier gas (flow rate of 40 ml/min); and a column oven temperature of 160–320° C. at a programmed increasing temperature rate of 7.5° C./min. The saccharide compositions of the reaction mixtures were tabulated in Table 1:

TABLE 1

| Substrate | Saccharide composition of reaction mixture (%) | | |
|---|---|---|---|
| | Trehalose | Glucose | Maltose |
| Maltose | 70.0 | 4.4 | 25.6 |
| Trehalose | 76.2 | 3.1 | 20.7 |

As is shown in Table 1, the purified enzyme formed about 70 w/w % trehalose and about 4 w/w % glucose when acted on maltose as a substrate, while it formed about 21 w/w % maltose and about 3 w/w % glucose when acted on trehalose as a substrate. These facts indicate that the purified enzyme has activities of converting maltose into trehalose and of converting trehalose into maltose, as well as of hydrolyzing α-1,4 linkage in maltose molecule and α, α-1, 1 linkage in trehalose molecule. There has been no report of such an enzyme, and this leads to an estimation of having a novel enzymatic pathway.

Experiment 2-2

Molecular Weight

In accordance with the method as reported by U. K. Laemmli in *Nature*, Vol.227, pp.680–685 (1970), the purified enzyme was electrophoresed on sodium dodecyl sulfate polyacrylamide gel electrophoresis (SDS-PAGE) to give a single protein band at a position corresponding to about 100,000–110,000 daltons. The marker proteins used in this experiment were myosin (MW=200,000 daltons), β-galactosidase (MW=116,250 daltons), phosphorylase B (MW=97,400 daltons), serum albumin (MW=66,200 daltons) and ovalbumin (MW=45,000 daltons).

Experiment 2-3

Isoelectric Point

The purified enzyme gave an isoelectric point of about 3.8–4.8 when isoelectrophoresed in 2 w/v % "AMPHOLINE®", a polyacrylamide gel commercialized by Pharmacia LKB Biotechnology AB, Uppsala, Sweden. cl Experiment 2-4

Optimum Temperature

The optimum temperature of the purified enzyme was about 65° C. as shown in FIG. 1 when incubated in usual manner in 10 mM phosphate buffer (pH 7.0) for 60 min.

Experiment 2-5

Optimum pH

Figure 2:
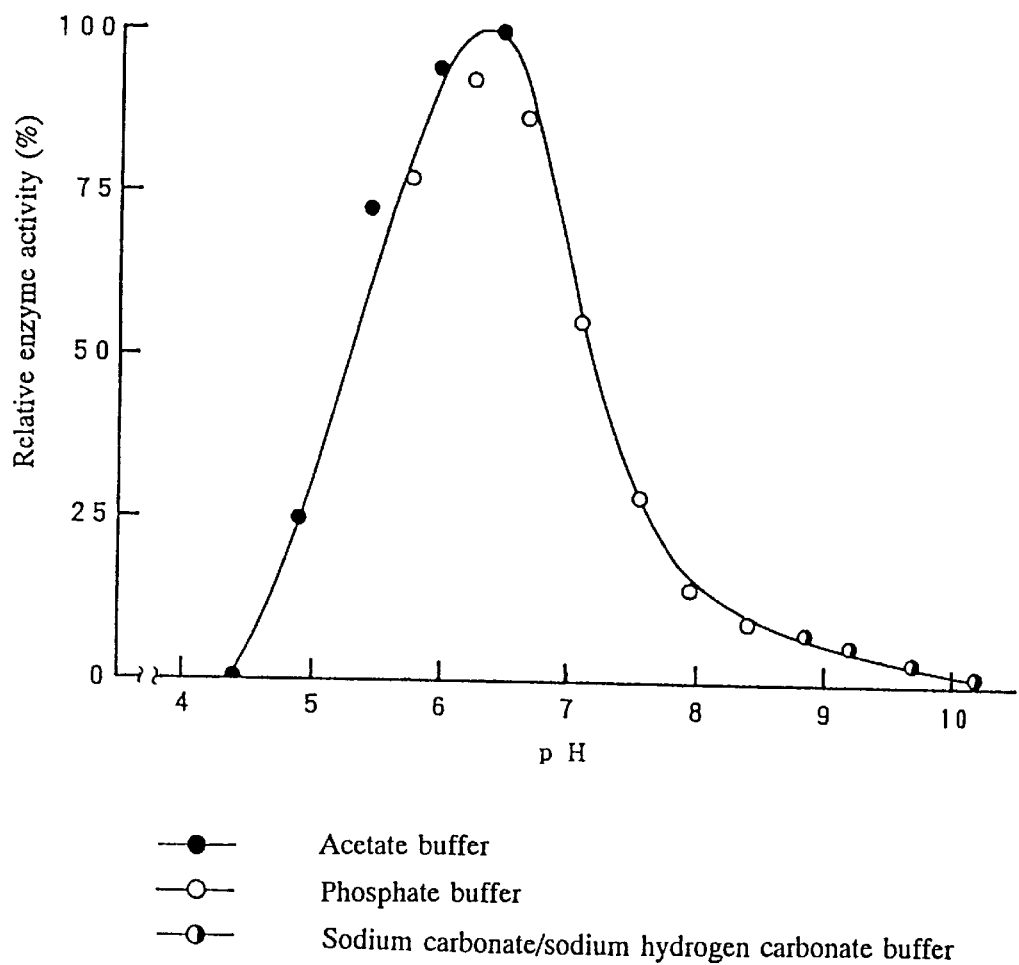
FIG. 2 shows the optimum pH of an enzyme produced from *Thermus aquaticus* (ATCC 33923).

The optimum pH of the purified enzyme was about 6.0–6.7 as shown in FIG. 2 when tested in usual manner by incubating it at 60° C. for 60 min in 10 mM acetate buffer, phosphate buffer or sodium carbonate/sodium hydrogen carbonate buffer with different pHs.

Experiment 2-6
Thermal Stability

Figure 3:
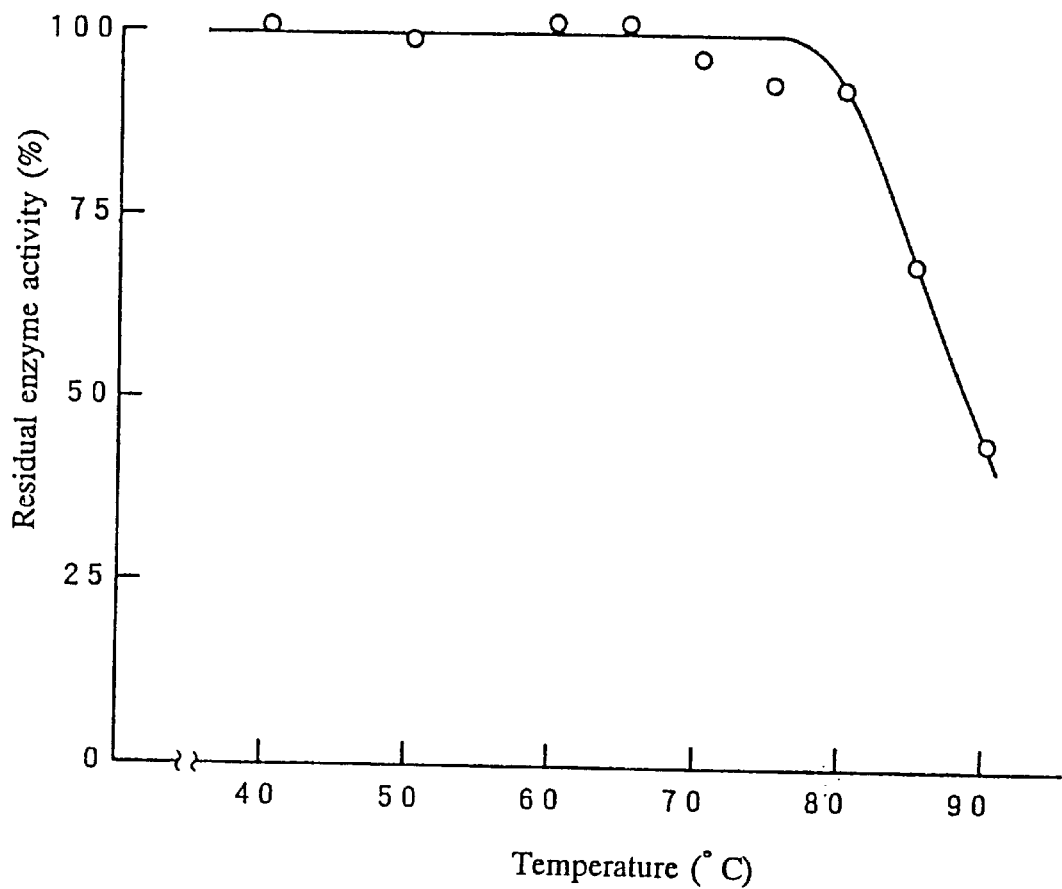
FIG. 3 shows the thermal stability of an enzyme produced from *Thermus aquaticus* (ATCC 33923).

The purified enzyme was stable up to a temperature of about 80° C. as shown in FIG. 3 when tested in usual manner by incubating it in 50 mM phosphate buffer (pH 7.0) for 60 min.

Experiment 2-7
pH Stability

Figure 4:
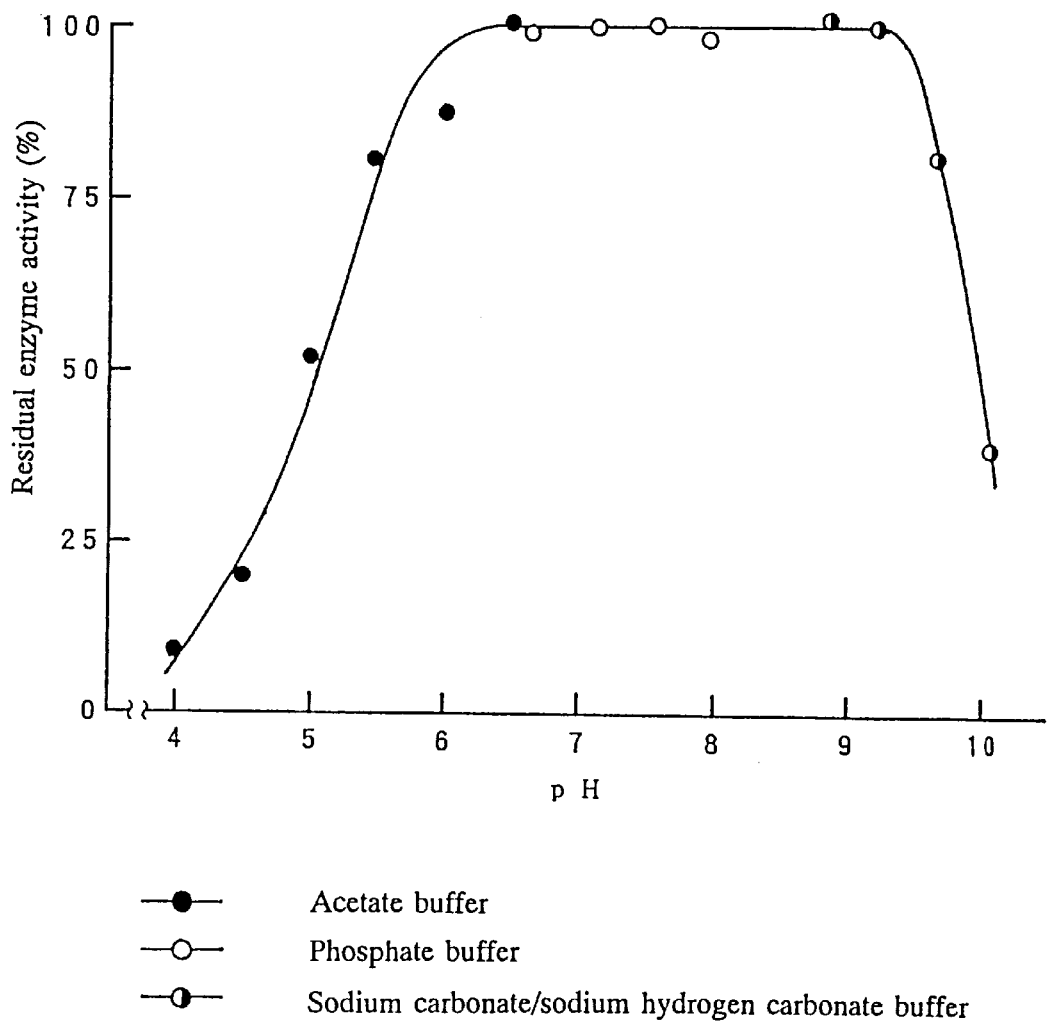
FIG. 4 shows the pH stability of an enzyme produced from *Thermus aquaticus* (ATCC 33923).

The purified enzyme was stable up to a pH of about 5.5–9.5 as shown in FIG. 4 when experimented in usual manner by incubating it at 60° C. for 60 min in 50 mM acetate buffer, phosphate buffer or sodium carbonate/sodium hydrogen carbonate buffer with different pHs.

Experiment 2-8
Amino Acid Sequence Containing the N-terminus

The amino acid sequence containing the N-terminus of the purified enzyme was analyzed on "MODEL 470A", a gas-phase protein sequencer commercialized by Perkin-Elmer Corp., Instrument Div., Norrwalk, USA, and revealed to have the amino acid sequence containing the N-terminus in SEQ ID NO:1.

```
SEQ ID NO:1:
Met Asp Pro Leu Trp Tyr Lys Asp Ala Val Ile Tyr Gln Leu His Val
1               5                   10                  15

Arg Ser Phe Phe
            20
```

Experiment 2-9
Partial Amino Acid Sequence

An adequate amount of the purified enzyme prepared in Experiment 1-2 was weighed, dialyzed against 10 mM Tris-HCl buffer (pH 9.0) at 4° C. for 18 hours, and admixed with 10 mM Tris-HCl buffer (pH 9.0) to obtain a solution containing about one mg/ml of the enzyme. The solution was incubated at 100° C. for 5 min to denature the enzyme, and about one ml of which was placed in a test tube, admixed with 40 μg lysyl endopeptidase, and incubated at 30° C. for 44 hours to partially hydrolyze the enzyme. The resultant hydrolysate was applied to "μBONDASPERE C18", a column for reverse-phase high-performance liquid chromatography commercialized by Japan Millipore Ltd., Tokyo, Japan, which had been equilibrated with 0.1 v/v % trifluoroacetate, followed by feeding to the column 0.1 v/v % trifluoroacetate containing acetonitrile at a flow rate of 1.0 ml/min while increasing the concentration of acetonitrile from 0 v/v % to 70 v/v %.

Fractions containing a peptide fragment eluted about 58 min to 60 min after the initiation of the feeding were collected, pooled, dried in vacuo, and dissolved in 0.5 ml of 10 mM Tris-HCl buffer (pH 8.0), admixed with 5 μg TPCK treated trypsin, and incubated at 37° C. for 16 hours to effect hydrolysis. The enzymatic reaction was suspended by freezing, and the resultant hydrolyzate was fed to a column packed with "μBONDASPERE C18", followed by feeding to the column 0.1 v/v % trifluoroacetate containing aqueous acetonitrile at a flow rate of 1.0 ml/min while increasing the concentration of aqueous acetonitrile from 15 v/v % to 55 v/v %. Fractions, containing a peptide fragment eluted about 42 min after the initiation of the feeding, were collected, pooled, dried in vacuo, and dissolved in 0.1 v/v trifluoroacetate containing 50 v/v % aqueous acetonitrile. Similarly as in Experiment 2-8, it was revealed that the peptide fragment contained the amino acid sequence in SEQ ID NO:2.

```
SEQ ID NO:2:
Ile Leu Leu Ala Glu Ala Asn Met Trp Pro Glu Glu
1               5                       10

Thr Leu Pro
        15
```

Since no enzyme with these physicochemical properties has been known, it can be estimated to be a novel substance.

The present inventors energetically screened the chromosomal DNA of *Thermus aquaticus* (ATCC 33923) by using an oligonucleotide as a probe which had been chemically synthesized based on the amino acid sequences as revealed in Experiments 2-8 and 2-9, and have obtained a DNA fragment which consisted of about 3,600 base pairs having the base sequence in SEQ ID NO:4. The decoding of the base sequence revealed that a thermostable enzyme from the microorganism consists of 963 amino acids and has the amino acid sequence in SEQ ID NO:3.

SEQ ID NO:3:

```
Met Asp Pro Leu Trp Tyr Lys Asp Ala Val Ile Tyr Gln Leu His Val
 1               5                  10                  15

Arg Ser Phe Phe Asp Ala Asn Asn Asp Gly Tyr Gly Asp Phe Glu Gly
            20                  25                  30

Leu Arg Arg Lys Leu Pro Tyr Leu Glu Glu Leu Gly Val Asn Thr Leu
        35                  40                  45

Trp Leu Met Pro Phe Phe Gln Ser Pro Leu Arg Asp Asp Gly Tyr Asp
 50              55                  60

Ile Ser Asp Tyr Tyr Gln Ile Leu Pro Val His Gly Thr Leu Glu Asp
 65                  70                  75                  80

Phe Thr Val Asp Glu Ala His Gly Arg Gly Met Lys Val Ile Ile Glu
                85                  90                  95

Leu Val Leu Asn His Thr Ser Ile Asp His Pro Trp Phe Gln Glu Ala
                100                 105                 110

Arg Lys Pro Asn Ser Pro Met Arg Asp Trp Tyr Val Trp Ser Asp Thr
        115                 120                 125

Pro Glu Lys Tyr Lys Gly Val Arg Val Ile Phe Lys Asp Phe Glu Thr
        130                 135                 140

Ser Asn Trp Thr Phe Asp Pro Val Ala Lys Ala Tyr Tyr Trp His Arg
145                 150                 155                 160

Phe Tyr Trp His Gln Pro Asp Leu Asn Trp Asp Ser Pro Glu Val Glu
                165                 170                 175

Lys Ala Ile His Gln Val Met Phe Phe Trp Ala Asp Leu Gly Val Asp
                180                 185                 190

Gly Phe Arg Leu Asp Ala Ile Pro Tyr Leu Tyr Glu Arg Glu Gly Thr
        195                 200                 205

Ser Cys Glu Asn Leu Pro Glu Thr Ile Glu Ala Val Lys Arg Leu Arg
210                 215                 220

Lys Ala Leu Glu Glu Arg Tyr Gly Pro Gly Lys Ile Leu Leu Ala Glu
225                 230                 235                 240

Ala Asn Met Trp Pro Glu Glu Thr Leu Pro Tyr Phe Gly Asp Gly Asp
                245                 250                 255

Gly Val His Met Ala Tyr Asn Phe Pro Leu Met Pro Arg Ile Phe Met
                260                 265                 270

Ala Leu Arg Arg Glu Asp Arg Gly Pro Ile Glu Thr Met Leu Lys Glu
        275                 280                 285

Ala Glu Gly Ile Pro Glu Thr Ala Gln Trp Ala Leu Phe Leu Arg Asn
        290                 295                 300

His Asp Glu Leu Thr Leu Glu Lys Val Thr Glu Glu Arg Glu Phe
305                 310                 315                 320

Met Tyr Glu Ala Tyr Ala Pro Asp Pro Lys Phe Arg Ile Asn Leu Gly
                325                 330                 335

Ile Arg Arg Arg Leu Met Pro Leu Leu Gly Gly Asp Arg Arg Arg Tyr
        340                 345                 350

Glu Leu Leu Thr Ala Leu Leu Leu Thr Leu Lys Gly Thr Pro Ile Val
        355                 360                 365

Tyr Tyr Gly Asp Glu Ile Gly Met Gly Asp Asn Pro Phe Leu Gly Asp
        370                 375                 380

Arg Asn Gly Val Arg Thr Pro Met Gln Trp Ser Gln Asp Arg Ile Val
385                 390                 395                 400

Ala Phe Ser Arg Ala Pro Tyr His Ala Leu Phe Leu Pro Pro Val Ser
                405                 410                 415
```

-continued

```
Glu Gly Pro Tyr Ser Tyr His Phe Val Asn Val Glu Ala Gln Arg Glu
        420                 425                 430

Asn Pro His Ser Leu Leu Ser Phe Asn Arg Arg Phe Leu Ala Leu Arg
            435                 440                 445

Asn Gln His Ala Lys Ile Phe Gly Arg Gly Ser Leu Thr Leu Leu Pro
        450                 455                 460

Val Glu Asn Arg Arg Val Leu Ala Tyr Leu Arg Glu His Glu Gly Glu
465                 470                 475                 480

Arg Val Leu Val Val Ala Asn Leu Ser Arg Tyr Thr Gln Ala Phe Asp
            485                 490                 495

Leu Pro Leu Glu Ala Tyr Gln Gly Leu Val Pro Val Glu Leu Phe Ser
        500                 505                 510

Gln Gln Pro Phe Pro Pro Val Glu Gly Arg Tyr Arg Leu Thr Leu Gly
        515                 520                 525

Pro His Gly Phe Ala Leu Phe Ala Leu Lys Pro Val Glu Ala Val Leu
        530                 535                 540

His Leu Pro Ser Pro Asp Trp Ala Glu Pro Ala Pro Glu Glu Ala
545                 550                 555                 560

Asp Leu Pro Arg Val His Met Pro Gly Gly Pro Glu Val Leu Leu Val
            565                 570                 575

Asp Thr Leu Val His Glu Arg Gly Arg Glu Leu Leu Asn Ala Leu
        580                 585                 590

Ala Gln Thr Leu Lys Glu Lys Ser Trp Leu Ala Leu Lys Pro Gln Lys
        595                 600                 605

Val Ala Leu Leu Asp Ala Leu Arg Phe Gln Lys Asp Pro Pro Leu Tyr
        610                 615                 620

Leu Thr Leu Leu Gln Leu Glu Asn His Arg Thr Leu Gln Val Ser Leu
625                 630                 635                 640

Pro Leu Leu Trp Ser Pro Gln Arg Arg Glu Gly Pro Gly Leu Phe Ala
            645                 650                 655

Arg Thr His Gly Gln Pro Gly Tyr Phe Tyr Glu Leu Ser Leu Asp Pro
            660                 665                 670

Gly Phe Tyr Arg Leu Leu Ala Arg Leu Lys Glu Gly Phe Glu Gly
            675                 680                 685

Arg Ser Leu Arg Ala Tyr Tyr Arg Gly Arg His Pro Gly Pro Val Pro
        690                 695                 700

Glu Ala Val Asp Leu Leu Arg Pro Gly Leu Ala Ala Gly Glu Gly Val
705                 710                 715                 720

Trp Val Gln Leu Gly Leu Val Gln Asp Gly Gly Leu Asp Arg Thr Glu
            725                 730                 735

Arg Val Leu Pro Arg Leu Asp Leu Pro Trp Val Leu Arg Pro Glu Gly
            740                 745                 750

Gly Leu Phe Trp Glu Arg Gly Ala Ser Arg Arg Val Leu Ala Leu Thr
        755                 760                 765

Gly Ser Leu Pro Pro Gly Arg Pro Gln Asp Leu Phe Ala Ala Leu Glu
        770                 775                 780

Val Arg Leu Leu Glu Ser Leu Pro Arg Leu Arg Gly His Ala Pro Gly
785                 790                 795                 800

Thr Pro Gly Leu Leu Pro Gly Ala Leu His Glu Thr Glu Ala Leu Val
            805                 810                 815

Arg Leu Leu Gly Val Arg Leu Ala Leu Leu His Arg Ala Leu Gly Glu
        820                 825                 830

Val Glu Gly Val Val Gly Gly His Pro Leu Leu Gly Arg Gly Leu Gly
        835                 840                 845
```

-continued

```
Ala Phe Leu Glu Leu Glu Gly Glu Val Tyr Leu Val Ala Leu Gly Ala
    850                 855                 860

Glu Lys Arg Gly Thr Val Glu Glu Asp Leu Ala Arg Leu Ala Tyr Asp
865                 870                 875                 880

Val Glu Arg Ala Val His Leu Ala Leu Glu Ala Leu Glu Ala Glu Leu
                885                 890                 895

Trp Ala Phe Ala Glu Val Ala Asp His Leu His Ala Phe Leu
            900                 905                 910

Gln Ala Tyr Arg Ser Ala Leu Pro Glu Glu Ala Leu Glu Glu Ala Gly
        915                 920                 925

Trp Thr Arg His Met Ala Glu Val Ala Ala Glu His Leu His Arg Glu
    930                 935                 940

Glu Arg Pro Ala Arg Lys Arg Ile His Glu Arg Trp Gln Ala Lys Ala
945                 950                 955                 960

Gly Lys Ala
```

SEQ ID NO:4:

```
GTGGACCCCC TCTGGTACAA GGACGCGGTG ATCTACCAGC TCCACGTCCG CTCCTTCTTT    60
GACGCCAACA ACGACGGCTA CGGGGACTTT GAGGGCCTGA GGCGGAAGCT TCCCTACCTG   120
GAGGAGCTCG GGGTCAACAC CCTCTGGCTC ATGCCCTTCT TCCAGTCCCC CTTGAGGGAC   180
GACGGGTACG ATATCTCCGA CTACTACCAG ATCCTCCCCG TCCACGGGAC CCTGGAGGAC   240
TTCACCGTGG ACGAGGCCCA CGGCCGGGGG ATGAAGGTGA TCATTGAGCT CGTCCTGAAC   300
CACACCTCCA TTGACCACCC TTGGTTCCAG GAGGCGAGGA AGCCGAATAG CCCCATGCGG   360
GACTGGTACG TGTGGAGCGA CACCCCGGAG AAGTACAAGG GGGTCCGGGT CATCTTCAAG   420
GACTTTGAAA CCTCCAACTG GACCTTTGAC CCCGTGGCCA AGGCCTACTA CTGGCACCGC   480
TTCTACTGGC ACCAGCCCGA CCTCAACTGG GACAGCCCCG AGGTGGAGAA GGCCATCCAC   540
CAGGTCATGT TCTTCTGGGC CGACCTGGGG GTGGACGGCT TCCGCCTGGA CGCCATCCCC   600
TACCTCTACG AGCGGGAGGG GACCTCCTGC GAGAACCTCC CCGAGACCAT TGAGGCGGTG   660
AAGCGCCTGA GGAAGGCCCT GGAGGAGCGC TACGGCCCCG GAAGATCCT CCTCGCCGAG    720
GCCAACATGT GGCCGGAGGA GACCCTCCCC TACTTCGGGG ACGGGGACGG GGTCCACATG   780
GCCTACAACT TCCCCCTGAT GCCCCGGATC TTCATGGCCC TAAGGCGGGA GGACCGGGGT   840
CCCATTGAAA CCATGCTCAA GGAGGCGGAG GGGATCCCCG AAACCGCCCA GTGGGCCCTC   900
TTCCTCCGCA ACCACGACGA GCTCACCCTG GAGAAGGTCA CGGAGGAGGA GCGGGAGTTC   960
ATGTACGAGG CCTACGCCCC CGACCCCAAG TTCCGCATCA ACCTGGGGAT CCGCCGCCGC  1020
CTCATGCCCC TCCTCGGGGG CGACCGCAGG CGGTACGAGC TCCTCACCGC CCTCCTCCTC  1080
ACCCTAAAGG GCACGCCCAT CGTCTACTAC GGGGACGAGA TCGGCATGGG GGACAACCCC  1140
TTCCTCGGGG ACCGGAACGG TGTCAGGACC CCCATGCAGT GGTCCCAAGA CCGCATCGTC  1200
GCCTTCTCCC GCGCCCCCTA CCACGCCCTC TTCCTTCCCC CCGTGAGCGA GGGGCCCTAC  1260
AGCTACCACT TCGTCAACGT GGAGGCCCAG CGGGAAAAAC CCCACTCCCT CCTGAGCTTC  1320
AACCGCCGCT TCCTCGCCCT GAGGAACCAG CACGCCAAGA TCTTCGGCCG GGGGAGCCTC  1380
ACCCTTCTCC CCGTGGAGAA CCGGCGCGTC CTCGCCTACC TGAGGGAGCA CGAGGGGGAG  1440
CGGGTCCTGG TGGTGGCCAA CCTCTCCCGC TACACCCAGG CCTTTGACCT CCCCTTGGAG  1500
GCCTACCAAG GCCTCGTCCC CGTGGAGCTC TTCTCGCAGC AACCCTTCCC CCCGGTGGAG  1560
```

-continued

```
GGGCGCTACC GCTTGACCCT GGGCCCCCAC GGCTTCGCCC TCTTCGCCCT GAAGCCCGTG  1620

GAGGCGGTGC TCCACCTCCC CTCCCCCGAC TGGGCCGAGG AGCCCGCCCC CGAGGAGGCC  1680

GACCTGCCCC GGGTCCACAT GCCCGGGGGG CCGGAGGTCC TCCTGGTGGA CACCCTGGTC  1740

CACGAAAGGG GGCGGGAGGA GCTCCTAAAC GCCCTCGCCC AGACCCTGAA GGAGAAGAGC  1800

TGGCTCGCCC TCAAGCCGCA GAAGGTGGCC CTCCTGGACG CCCTCCGCTT CCAGAAGGAC  1860

CCGCCCCTTT ACCTCACCCT GCTCCAGCTG GAGAACCACA GGACCCTCCA GGTCTCCCTC  1920

CCCCTCCTCT GGTCCCCCCA GAGGCGGGAA GGCCCCGGCC TCTTCGCCCG CACCCACGGC  1980

CAGCCCGGCT ACTTCTACGA GCTCTCCTTG GACCCAGGCT TCTACCGCCT CCTCCTCGCC  2040

CGCCTTAAGG AGGGGTTTGA GGGGCGGAGC CTCCGGGCCT ACTACCGCGG CCGCCACCCG  2100

GGTCCCGTGC CCGAGGCCGT GGACCTCCTC CGGCCGGGAC TCGCGGCGGG GGAGGGGGTC  2160

TGGGTCCAGC TCGGCCTCGT CCAAGACGGG GGCCTGGACC GCACGGAGCG GGTCCTCCCC  2220

CGCCTGGACC TCCCCTGGGT TCTCCGGCCC GAAGGGGGCC TCTTCTGGGA GCGGGCGCC  2280

TCCAGAAGGG TCCTCGCCCT CACGGGAAGC CTCCCCCCGG GCCGCCCCCA GGACCTCTTC  2340

GCCGCCCTGG AGGTCCGGCT CCTGGAAAGC CTTCCCCGCC TCCGGGGCA CGCCCCCGGG  2400

ACCCCAGGCC TCCTTCCCGG GGCCCTGCAC GAGACCGAAG CCCTGGTCCG CCTCCTCGGG  2460

GTGCGCCTCG CCCTCCTCCA CCGGGCCCTT GGGGAGGTGG AGGGGGTGGT GGGGGGCCAC  2520

CCCCTCCTAG GCCGCGGCCT CGGGGCCTTC CTGGAGCTGG AGGGGGAGGT GTACCTCGTG  2580

GCCCTGGGCG CGGAAAAGCG GGGCACGGTG GAGGAGGACC TGGCCCGCCT GGCCTACGAC  2640

GTGGAGCGGG CCGTGCACCT CGCCCTCGAG GCCCTGGAGG CGGAGCTTTG GGCCTTTGCC  2700

GAGGAGGTGG CCGACCACCT CCACGCCGCC TTCCTCCAAG CCTACCGCTC CGCCCTCCCC  2760

GAGGAGGCCC TGGAGGAGGC GGGCTGGACG CGGCACATGG CCGAGGTGGC GGCGGAGCAC  2820

CTCCACCGGG AGGAAAGGCC CGCCCGCAAG CGCATCCACG AGCGCTGGCA GGCCAAGGCC  2880

GGAAAAGCC                                                          2889
```

The sequential experimental steps used to reveal the amino acid sequence and the base sequence in SEQ ID NOs:3 and 4 are summarized in the below:

(1) A thermostable enzyme was isolated from a culture of a donor microorganism, highly purified, and determined for its amino acid sequence containing the N-terminus. The purified enzyme was partially hydrolyzed with protease, and from which a peptide fragment was isolated and determined for its amino acid sequence;

(2) Separately, a chromosomal DNA was isolated from a donor microorganism's cell, purified and partially digested with a restriction enzyme to obtain a DNA fragment consisting of about 4,000–8,000 base pairs. The DNA fragment was ligated with a DNA ligase to a plasmid vector, which had been previously cut with a restriction enzyme, to obtain a recombinant DNA;

(3) The recombinant DNA was introduced into a microorganism of the species *Escherichia coli* to obtain transformants, and from which an objective transformant containing a DNA encoding the thermostable enzyme was selected by the colony hybridization method using an oligonucleotide, as a probe, which had been chemically synthesized based on the aforesaid partial amino acid sequence; and (4) The recombinant DNA was obtained from the selected transformant and annealed with a primer, followed by allowing a DNA polymerase to act on the resultant to extend the primer, and determining the base sequence of the resultant complementary chain DNA by the dideoxy chain termination method. The comparison of an amino acid sequence, which could be estimated based on the determined base sequence, with the aforesaid amino acid sequence concluded that it encodes the thermostable enzyme.

The following Experiments 3 and 4 concretely illustrate the above items (2) to (4), and the techniques used therein were conventional ones commonly used in this field, for example, those described by J. Sumbruck et al. in *"Molecular Cloning A Laboratory Manual"*, 2nd edition, published by Cold Spring Harbor Laboratory Press (1989).

EXPERIMENT 3

Preparation of Recombinant DNA Containing DNA Encoding Thermostable Enzyme, and Transformant

Experiment 3-1
Preparation of Chromosomal DNA

A seed culture of *Thermus aquaticus* (ATCC 33923) was inoculated into nutrient broth medium (pH 7.0), and cultured at 60° C. for 24 hours with a rotary shaker. The cells were separated from the resultant culture by centrifugation, suspended in TES buffer (pH 8.0), admixed with 0.05 w/v % lysozyme, and incubated at 37° C. for 30 min. The resultant was freezed at −80° C. for one hour, admixed with TSS buffer (pH 9.0), heated to 60° C., and further admixed with a mixture solution of TES buffer and phenol, and the resultant solution was chilled with ice, followed by centrifugation to obtain a supernatant. To the supernatant was added 2-fold volumes of cold ethanol, and the precipitated crude chromosomal DNA was collected, suspended in SSC buffer (pH 7.1), admixed with 7.5 μg ribonuclease and 125 μg protease, and incubated at 37° C. for one hour. Thereafter, a mixture solution of chloroform and isoamyl alcohol was added to the reaction mixture to extract the objective chromosomal DNA, and the extract was admixed with cold ethanol, followed by collecting the formed sediment containing the chromosomal DNA. The resultant purified chromosomal DNA was dissolved in SSC buffer (pH 7.1) to give a concentration of about one mg/ml, and the resultant solution was freezed at −80° C.

Experiment 3-2
Preparation of Recombinant DNA pBTM22 and Transformant BTM22

About one ml of the purified chromosomal DNA obtained in Example 3-1 was placed in a test tube, admixed with about 10 units of Sau 3AI, a restriction enzyme, and enzymatically reacted at 37° C. for about 20 min to partially cleave the chromosomal DNA, followed by recovering a DNA fragment consisting of about 4,000–8,000 base pairs by means of sucrose density-gradient ultracentrifugation. One μg of Bluescript II SK(+), a plasmid vector commercialized by Stratagene Cloning Systems, California, USA, was placed in a test tube, subjected to the action of Bam HI, a restriction enzyme, to completely digest the plasmid vector, admixed with 10 μg of the DNA fragment and 2 units of T4 DNA ligase, and allowed to stand at 4° C. overnight to ligate the DNA fragment to the plasmid vector fragment. To the resultant recombinant DNA was added 30 μl of "Epicurian Coli® XLI-Blue", a competent cell commercialized by Stratagene Cloning Systems, California, USA, Japan, allowed to stand under ice-chilling conditions for 30 min, heated to 42° C., admixed with SOC broth, and incubated at 37° C. for one hour to introduce the recombinant DNA into *Escherichia coli*.

The resultant transformant was inoculated into agar plate (pH 7.0) containing 50 μg/ml of 5-bromo-4-chloro-3-indolyl-β-galactoside, and cultured at 37° C. for 18 hours, followed by placing a nylon film on the agar plate to fix thereon about 6,000 colonies formed on the agar plate. Based on the amino acid sequence of Trp-Tyr-Lys-Asp-Ala-Val as shown in SEQ ID NO:1 (amino acid residues 5–10), the base sequence of probe 1 represented by the base sequence of 5'-TGGTAYAARGAYGCNGT-3' was chemically synthesized, labelled with $^{32}$P, and hybridized with the colonies of transformants fixed on the nylon film, followed by selecting 5 transformants which had strongly hybridized with the probe 1.

The objective recombinant DNA was selected in usual manner from the 5 transformants, and, in accordance with the method described by E. M. Southern in *Journal of Molecular Biology*, Vol.98, pp.503–517 (1975), the recombinant DNA was hybridized with probe 2 represented by the base sequence of 5'-AAYATGTGGCCNGARGA-3'(SEQ ID NO:8), which had been chemically synthesized based on the amino acid sequence in SEQ ID NO:2, i.e. Asn-Met-Trp-Pro-Glu-Glu (amino acid residues 7–12), and labelled with $^{32}$P, followed by selecting a recombinant DNA which had strongly hybridized with the probe 2. The recombinant DNA and the transformant thus selected were respectively named "pBTM22" and "BTM22".

Figure 5:
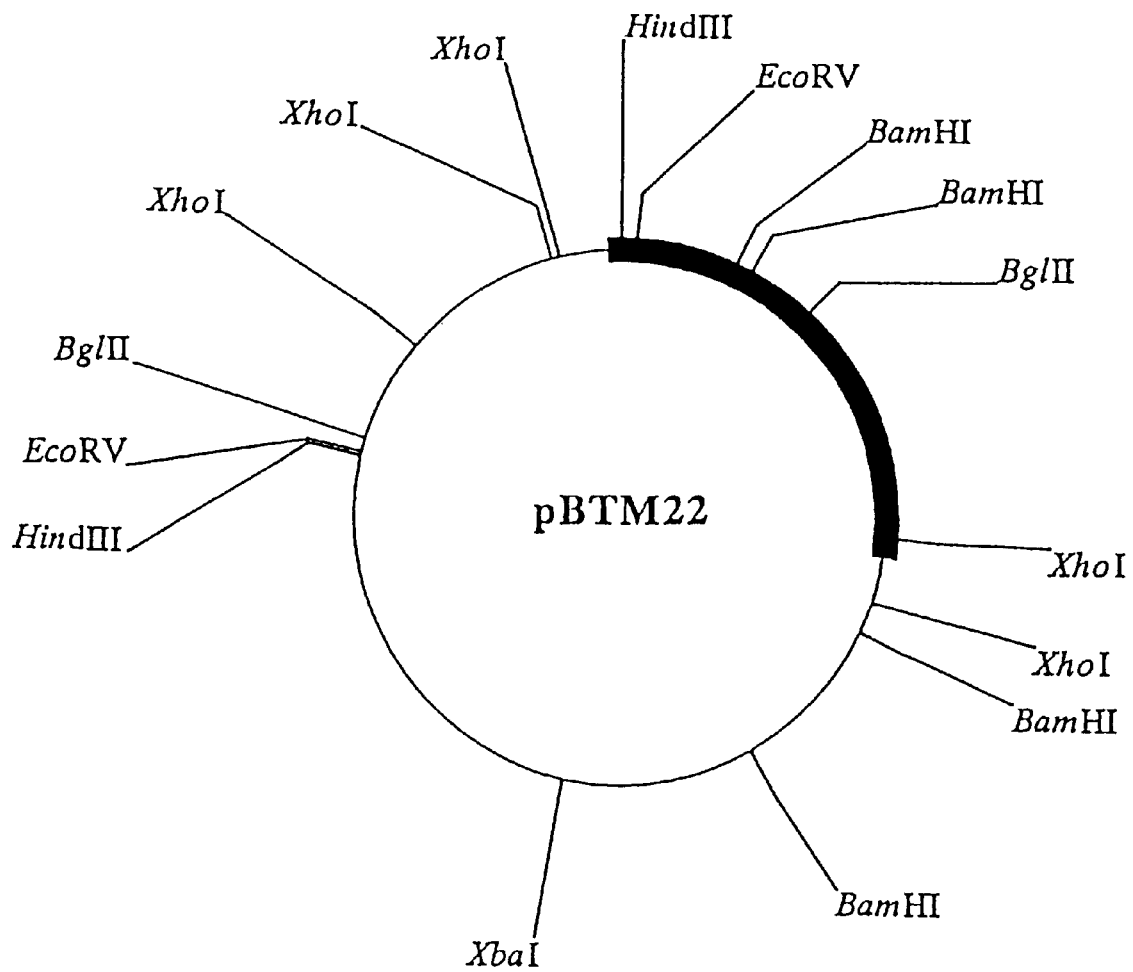
FIG. 5 shows the structure of the recombinant DNA pBTM22 according to the present invention.

The transformant BTM22 was inoculated into L-broth (pH 7.0) containing 100 μg/ml ampicillin, and cultured at 37° C. for 24 hours by a rotary shaker. After completion of the culture, the resultant cells were centrifugally collected from the culture, and treated with conventional alkaline method to extract a recombinant DNA from the cells. The extract was in usual manner purified and analyzed and revealing that the recombinant DNA pBTM22 consists of about 10,300 base pairs. As is shown in FIG. 5, a fragment containing a DNA, which consists of about 2,900 base pairs and encodes the thermostable enzyme, is located in the downstream near the digested site of Hind III, a restriction enzyme.

Experiment 3-3
Production of Recombinant Enzyme by Transformant BTM22

In 500-ml flasks were placed 100 ml aliquots of a liquid nutrient culture medium (pH 7.0) consisting of 2.0 w/v % glucose, 0.5 w/v % peptone, 0.1 w/v % yeast extract, 0.1 w/v % dipotassium hydrogen phosphate, 0.06 w/v % sodium dihydrogen phosphate, 0.05 w/v % magnesium sulfate heptahydrate, 0.5 w/v % calcium carbonate and water, and each flasks was sterilized by heating at 115° C. for 30 min, cooled, admixed with 50 μg/ml ampicillin, and inoculated with the transformant BTM22 obtained in Experiment 3-2, followed by culturing the transformant at 37° C. for 24 hours by a rotary shaker. The resultant culture was treated with an ultrasonic disintegrator to disrupt cells, and the resultant suspension was centrifuged to remove insoluble substances. The supernatant thus obtained was assayed for the enzyme activity and revealing that one L of the culture contained about 800 units of a recombinant enzyme.

As a control, a seed culture of *Escherichia coli* XLI-Blue or *Thermus aquaticus* (ATCC 33923) was inoculated in a fresh preparation of the same liquid nutrient culture medium but free of ampicillin, and, in the case of culturing *Thermus aquaticus* (ATCC 33923), it was cultured and treated similarly as above except that the cultivation temperature was set to 65° C. Assaying the activity of the resultant, one L culture of *Thermus aquaticus* contained about 350 units of the enzyme, and the yield was significantly lower than that of transformant BTM22. *Escherichia coli* XLI-Blue used as a host did not form the thermostable enzyme.

Thereafter, the enzyme produced by the transformant BTM22 was purified similarly as in Experiments 1 and 2, and examined for its physicochemical properties and features. As a result, it was revealed that it has substantially the same physicochemical properties as the thermostable enzyme of *Thermus aquaticus* (ATCC 33923), i.e. it has a molecular weight of about 100,000–110,000 daltons on SDS-PAGE and an isoelectric point of about 3.8–4.8 on isoelectrophoresis, and is not substantially inactivated even when incubated at 80° C. for 60 min in water (pH 7.0). The results indicate that the present thermostable enzyme can be prepared by recombinant DNA technology, and the yield can be significantly increased thereby.

EXPERIMENT 4
Preparation of Complementary Chain DNA and Determination for its Base Sequence and Amino Acid Sequence Two µg of the recombinant DNA pBTM22 in Experiment 3-2 was placed in a test tube, admixed with 2 M aqueous sodium hydroxide solution to effect degeneration, and admixed with an adequate amount of cold ethanol, followed by collecting the formed sediment containing a template DNA and drying the sediment in vacuo. To the template DNA were added 50 pmole/ml of a chemically synthesized primer represented by the base sequence of 5'-GTAAAACGACGGCCAGT-3'(SEQ ID NO:9), 10 µl of 40 mM Tris-HCl buffer (pH 7.5) containing 20 mM magnesium chloride and 20 mM sodium chloride, and the mixture was incubated at 65° C. for 2 min to effect annealing and admixed with 2 µl of an aqueous solution containing dATP, dGTP and dTTP in respective amounts of 7.5 µM, 0.5 µl of [α-$^{32}$P]dCTP (2 mCi/ml), one µl of 0.1 M dithiothreitol, and 2 µl of 1.5 units/ml T7 DNA polymerase, followed by incubating the resultant mixture at 25° C. for 5 min to extend the primer from the 5'-terminus to the 3'-terminus. Thus, a complementary chain DNA was formed.

The reaction product containing the complementary chain DNA was divided into four equal parts, to each of which 2.5 µl of 50 mM aqueous sodium chloride solution containing 80 µM dNTP and 8 µM ddATP, ddCTP, ddGTP or ddTTP was added, and the resultant mixture was incubated at 37° C. for 5 min, followed by suspending the reaction by the addition of 4 µl of 98 v/v % aqueous formamide solution containing 20 mM EDTA, 0.05 w/v % bromophenol blue, and 0.05 w/v % xylene cyanol. The reaction mixture was heated with a boiling-water bath for 3 min, and a small portion of which was placed on a 6 w/v % polyacrylamide gel, and electrophoresed by energizing it with a constant voltage of about 2,000 volts to separate DNA fragments, followed by fixing the gel in usual manner, drying it and subjecting the resultant to autoradiography.

Analyses of the DNA fragments separated on the radiogram revealed that the complementary chain DNA contains the base sequence consisting of about 3,600 base pairs in SEQ ID NO:5. An amino acid sequence estimable from the base sequence was as shown in parallel in SEQ ID NO:5, and it was compared with the amino acid sequence containing the N-terminus or the partial amino acid sequences in SEQ ID NOs:1 and 2 and revealing that the amino acid sequence in SEQ ID NO:1 corresponded to that positioning from 1 to 20 in SEQ ID NO:5, and the amino acid sequence in SEQ ID NO:2 corresponded to that positioning from 236 to 250 in SEQ ID NO:5. These results indicate that the present recombinant enzyme has the amino acid sequence in SEQ ID NO:3, and the amino acid sequence (SEQ ID NO:3), of the DNA derived from *Thermus aquaticus* (ATCC 33923) is encoded by the base sequence in SEQ ID NO:4.

```
SEQ ID NO:5:

GCCCCTCCCT CCCCCAACCG GGCCTTCCCG TGGGGGGGGG GCACAGCCTG GAGGAAGGGG   60

TGCTCGACGG GGAGGTGCGG CCCCTCTTGC GCCGTGGGCC GTGACCCCTT GCGGGCCAGG  120

CTTCCCTCCT ACCCCGGGGT GCGGGTGGAG GACAAGGGCT TCGCCCTGGC CCTGCACTAC  180

CGGGGGGCGG AGGGCGAGGA GAAGGCCCGG GCCTGCCTCG AGGCCTGGCT TAAGGCGGTG  240

GAGGGGCTCC TGGGGGCCTT GGGCCTCGAG GCCCTCCCCG GCAAGAGGGT CCTGGAGCTC  300

AAGCCCAAGG GGGTGGACAA GGGCCAAGCG GTCCTCAGGC TCCTCGGACG CCACCCGGAC  360

CACACCCCCG TTTACATCGG GGACGACACC ACCGACGAGG CCGCCTTCCT CGCCTTAAGG  420

GGCCGGGGCC TCACCTTCAA GGTGGGGGAA GGCCCCACGG CGGCCCAAGG CCGGCTCAAG  480

GACGTGGAGG AGGTCCTGGC CTACTTGCAA ACCTACCTCC GACCCACTAG CCTTTAGGCC  540

GTG GAC CCC CTC TGG TAC AAG GAC GCG GTG ATC TAC CAG CTC CAC GTC    588
Met Asp Pro Leu Trp Tyr Lys Asp Ala Val Ile Tyr Gln Leu His Val
1               5                   10                  15

CGC TCC TTC TTT GAC GCC AAC AAC GAC GGC TAC GGG GAC TTT GAG GGC    636
Arg Ser Phe Phe Asp Ala Asn Asn Asp Gly Tyr Gly Asp Phe Glu Gly
                20                  25                  30

CTG AGG CGG AAG CTT CCC TAC CTG GAG GAG CTC GGG GTC AAC ACC CTC    684
Leu Arg Arg Lys Leu Pro Tyr Leu Glu Glu Leu Gly Val Asn Thr Leu
            35                  40                  45

TGG CTC ATG CCC TTC TTC CAG TCC CCC TTG AGG GAC GAC GGG TAC GAT    732
Trp Leu Met Pro Phe Phe Gln Ser Pro Leu Arg Asp Asp Gly Tyr Asp
        50                  55                  60

ATC TCC GAC TAC TAC CAG ATC CTC CCC GTC CAC GGG ACC CTG GAG GAC    780
Ile Ser Asp Tyr Tyr Gln Ile Leu Pro Val His Gly Thr Leu Glu Asp
65                  70                  75                  80
```

-continued

| | |
|---|---|
| TTC ACC GTG GAC GAG GCC CAC GGC CGG GGG ATG AAG GTG ATC ATT GAG<br>Phe Thr Val Asp Glu Ala His Gly Arg Gly Met Lys Val Ile Ile Glu<br>                     85                    90                 95 | 828 |
| CTC GTC CTG AAC CAC ACC TCC ATT GAC CAC CCT TGG TTC CAG GAG GCG<br>Leu Val Leu Asn His Thr Ser Ile Asp His Pro Trp Phe Gln Glu Ala<br>               100               105               110 | 876 |
| AGG AAG CCG AAT AGC CCC ATG CGG GAC TGG TAC GTG TGG AGC GAC ACC<br>Arg Lys Pro Asn Ser Pro Met Arg Asp Trp Tyr Val Trp Ser Asp Thr<br>             115               120               125 | 924 |
| CCG GAG AAG TAC AAG GGG GTC CGG GTC ATC TTC AAG GAC TTT GAA ACC<br>Pro Glu Lys Tyr Lys Gly Val Arg Val Ile Phe Lys Asp Phe Glu Thr<br>       130                135               140 | 972 |
| TCC AAC TGG ACC TTT GAC CCC GTG GCC AAG GCC TAC TAC TGG CAC CGC<br>Ser Asn Trp Thr Phe Asp Pro Val Ala Lys Ala Tyr Tyr Trp His Arg<br>145               150               155               160 | 1020 |
| TTC TAC TGG CAC CAG CCC GAC CTC AAC TGG GAC AGC CCC GAG GTG GAG<br>Phe Tyr Trp His Gln Pro Asp Leu Asn Trp Asp Ser Pro Glu Val Glu<br>               165               170               175 | 1068 |
| AAG GCC ATC CAC CAG GTC ATG TTC TTC TGG GCC GAC CTG GGG GTG GAC<br>Lys Ala Ile His Gln Val Met Phe Phe Trp Ala Asp Leu Gly Val Asp<br>             180               185               190 | 1116 |
| GGC TTC CGC CTG GAC GCC ATC CCC TAC CTC TAC GAG CGG GAG GGG ACC<br>Gly Phe Arg Leu Asp Ala Ile Pro Tyr Leu Tyr Glu Arg Glu Gly Thr<br>       195                200               205 | 1164 |
| TCC TGC GAG AAC CTC CCC GAG ACC ATT GAG GCG GTG AAG CGC CTG AGG<br>Ser Cys Glu Asn Leu Pro Glu Thr Ile Glu Ala Val Lys Arg Leu Arg<br>       210                215               220 | 1212 |
| AAG GCC CTG GAG GAG CGC TAC GGC CCC GGG AAG ATC CTC CTC GCC GAG<br>Lys Ala Leu Glu Glu Arg Tyr Gly Pro Gly Lys Ile Leu Leu Ala Glu<br>225               230               235               240 | 1260 |
| GCC AAC ATG TGG CCG GAG GAG ACC CTC CCC TAC TTC GGG GAC GGG GAC<br>Ala Asn Met Trp Pro Glu Glu Thr Leu Pro Tyr Phe Gly Asp Gly Asp<br>             245               250               255 | 1308 |
| GGG GTC CAC ATG GCC TAC AAC TTC CCC CTG ATG CCC CGG ATC TTC ATG<br>Gly Val His Met Ala Tyr Asn Phe Pro Leu Met Pro Arg Ile Phe Met<br>             260               265               270 | 1356 |
| GCC CTA AGG CGG GAG GAC CGG GGT CCC ATT GAA ACC ATG CTC AAG GAG<br>Ala Leu Arg Arg Glu Asp Arg Gly Pro Ile Glu Thr Met Leu Lys Glu<br>       275                280               285 | 1404 |
| GCG GAG GGG ATC CCC GAA ACC GCC CAG TGG GCC CTC TTC CTC CGC AAC<br>Ala Glu Gly Ile Pro Glu Thr Ala Gln Trp Ala Leu Phe Leu Arg Asn<br>             290               295               300 | 1452 |
| CAC GAC GAG CTC ACC CTG GAG AAG GTC ACG GAG GAG GAG CGG GAG TTC<br>His Asp Glu Leu Thr Leu Glu Lys Val Thr Glu Glu Glu Arg Glu Phe<br>305               310               315               320 | 1500 |
| ATG TAC GAG GCC TAC GCC CCC GAC CCC AAG TTC CGC ATC AAC CTG GGG<br>Met Tyr Glu Ala Tyr Ala Pro Asp Pro Lys Phe Arg Ile Asn Leu Gly<br>             325               330               335 | 1548 |

-continued

```
ATC CGC CGC CGC CTC ATG CCC CTC CTC GGG GGC GAC CGC AGG CGG TAC    1596
Ile Arg Arg Arg Leu Met Pro Leu Leu Gly Gly Asp Arg Arg Arg Tyr
            340                 345                 350

GAG CTC CTC ACC GCC CTC CTC CTC ACC CTA AAG GGC ACG CCC ATC GTC    1644
Glu Leu Leu Thr Ala Leu Leu Leu Thr Leu Lys Gly Thr Pro Ile Val
            355                 360                 365

TAC TAC GGG GAC GAG ATC GGC ATG GGG GAC AAC CCC TTC CTC GGG GAC    1692
Tyr Tyr Gly Asp Glu Ile Gly Met Gly Asp Asn Pro Phe Leu Gly Asp
            370                 375                 380

CGG AAC GGT GTC AGG ACC CCC ATG CAG TGG TCC CAA GAC CGC ATC GTC    1740
Arg Asn Gly Val Arg Thr Pro Met Gln Trp Ser Gln Asp Arg Ile Val
385                 390                 395                 400

GCC TTC TCC CGC GCC CCC TAC CAC GCC CTC TTC CTT CCC CCC GTG AGC    1788
Ala Phe Ser Arg Ala Pro Tyr His Ala Leu Phe Leu Pro Pro Val Ser
            405                 410                 415

GAG GGG CCC TAC AGC TAC CAC TTC GTC AAC GTG GAG GCC CAG CGG GAA    1836
Glu Gly Pro Tyr Ser Tyr His Phe Val Asn Val Glu Ala Gln Arg Glu
            420                 425                 430

AAC CCC CAC TCC CTC CTG AGC TTC AAC CGC CGC TTC CTC GCC CTG AGG    1884
Asn Phe His Ser Leu Leu Ser Phe Asn Arg Arg Phe Leu Ala Leu Arg
            435                 440                 445

AAC CAG CAC GCC AAG ATC TTC GGC CGG GGG AGC CTC ACC CTT CTC CCC    1932
Asn Gln His Ala Lys Ile Phe Gly Arg Gly Ser Leu Thr Leu Leu Pro
            450                 455                 460

GTG GAG AAC CGG CGC GTC CTC GCC TAC CTG AGG GAG CAC GAG GGG GAG    1980
Val Glu Asn Arg Arg Val Leu Ala Tyr Leu Arg Glu His Glu Gly Glu
465                 470                 475                 480

CGG GTC CTG GTG GTG GCC AAC CTC TCC CGC TAC ACC CAG GCC TTT GAC    2028
Arg Val Leu Val Val Ala Asn Leu Ser Arg Tyr Thr Gln Ala Phe Asp
            485                 490                 495

CTC CCC TTG GAG GCC TAC CAA GGC CTC GTC CCC GTG GAG CTC TTC TCG    2076
Leu Pro Leu Glu Ala Tyr Gln Gly Leu Val Pro Val Glu Leu Phe Ser
            500                 505                 510

CAG CAA CCC TTC CCC CCG GTG GAG GGG CGC TAC CGC TTG ACC CTG GGC    2124
Gln Gln Pro Phe Pro Pro Val Glu Gly Arg Tyr Arg Leu Thr Leu Gly
            515                 520                 525

CCC CAC GGC TTC GCC CTC TTC GCC CTG AAG CCC GTG GAG GCG GTG CTC    2172
Pro His Gly Phe Ala Leu Phe Ala Leu Lys Pro Val Glu Ala Val Leu
            530                 535                 540

CAC CTC CCC TCC CCC GAC TGG GCC GAG GAG CCC GCC CCC GAG GAG GCC    2220
His Leu Pro Ser Pro Asp Trp Ala Glu Glu Pro Ala Pro Glu Glu Ala
545                 550                 555                 560

GAC CTG CCC CGG GTC CAC ATG CCC GGG GGG CCG GAG GTC CTC CTG GTG    2268
Asp Leu Pro Arg Val His Met Pro Gly Gly Pro Glu Val Leu Leu Val
            565                 570                 575

GAC ACC CTG GTC CAC GAA AGG GGG CGG GAG GAG CTC CTA AAC GCC CTC    2316
Asp Thr Leu Vla His Glu Arg Gly Arg Glu Glu Leu Leu Asn Ala Leu
            580                 585                 590
```

```
                                    -continued
GCC CAG ACC CTG AAG GAG AAG AGC TGG CTC GCC CTC AAG CCG CAG AAG    2364

Ala Gln Thr Leu Lys Glu Lys Ser Trp Leu Ala Leu Lys Pro Gln Lys
        595                 600                 605

GTG GCC CTC CTG GAC GCC CTC CGC TTC CAG AAG GAC CCG CCC CTT TAC    2412

Val Ala Leu Leu Asp Ala Leu Arg Phe Gln Lys Asp Pro Pro Lys Tyr
    610                 615                 620

CTC ACC CTG GTC CAG CTG GAG AAC CAC AGG ACC CTC CAG GTC TCC CTC    2460

Leu Thr Leu Val Gln Leu Glu Asn His Arg Thr Leu Gln Val Ser Leu
625                 630                 635                 640

CCC CTC CTC TGG TCC CCC CAG AGG CGG GAA GGC CCC GGC CTC TTC GCC    2508

Pro Leu Leu Trp Ser Pro Gln Arg Arg Glu Gly Pro Gly Leu Phe Ala
                645                 650                 655

CGC ACC CAC GGC CAG CCC GGC TAC TTC TAC GAG CTC TCC TTG GAC CCA    2556

Arg Thr His Gly Gln Pro Gly Tyr Phe Tyr Glu Leu Ser Leu Asp Pro
            660                 665                 670

GGC TTC TAC CGC CTC CTC CTC GCC CGC CTT AAG GAG GGG TTT GAG GGG    2604

Gly Phe Tyr Arg Leu Leu Leu Ala Arg Leu Lys Glu Gly Phe Glu Gly
        675                 680                 685

CGG AGC CTC CGG GCC TAC TAC CGC GGC CGC CAC CCG GGT CCC GTG CCC    2652

Arg Ser Leu Arg Ala Tyr Tyr Arg Gly Arg His Pro Gly Pro Val Pro
    690                 695                 700

GAG GCC GTG GAC CTC CTC CGG CCG GGA CTC GCG GCG GGG GAG GGG GTC    2700

Glu Ala Val Asp Leu Leu Arg Pro Gly Leu Ala Ala Gly Glu Gly Val
705                 710                 715                 720

TGG GTC CAG CTC GGC CTC GTC CAA GAC GGG GGC CTG GAC CGC ACG GAG    2748

Trp Val Gln Leu Gly Leu Val Gln Asp Gly Gly Leu Asp Arg Thr Glu
                725                 730                 735

CGG GTC CTC CCC CGC CTG GAC CTC CCC TGG GTT CTC CGG CCC GAA GGG    2796

Arg Val Leu Pro Arg Leu Asp Leu Pro Trp Val Leu Arg Pro Glu Gly
            740                 745                 750

GGC CTC TTC TGG GAG CGG GGC GCC TCC AGA AGG GTC CTC GCC CTC ACG    2844

Gly Leu Phe Trp Glu Arg Gly Ala Ser Arg Arg Val Leu Ala Leu Thr
        755                 760                 765

GGA AGC CTC CCC CCG GGC CGC CCC CAG GAC CTC TTC GCC GCC CTG GAG    2892

Gly Ser Leu Pro Pro Gly Arg Pro Gln Asp Leu Phe Ala Ala Leu Glu
    770                 775                 780

GTC CGG CTC CTG GAA AGC CTT CCC CGC CTC CGG GGG CAC GCC CCC GGG    2940

Val Arg Leu Leu Glu Ser Leu Pro Arg Leu Arg Gly His Ala Pro Gly
785                 790                 795                 800

ACC CCA GGC CTC CTT CCC GGG GCC CTG CAC GAG ACC GAA GCC CTG GTC    2988

Thr Pro Gly Leu Leu Pro Gly Ala Leu His Glu Thr Glu Ala Leu Val
                805                 810                 815

CGC CTC CTC GGG GTG CGC CTC GCC CTC CTC CAC CGG GCC CTT GGG GAG    3036

Arg Leu Leu Gly Val Arg Leu Ala Leu Leu His Arg Ala Leu Gly Glu
            820                 825                 830

GTG GAG GGG GTG GTG GGG GGC CAC CCC CTC CTA GGC CGC GGC CTC GGG    3084

Val Glu Gly Val Val Gly Gly His Pro Leu Leu Gly Arg Gly Leu Gly
        835                 840                 845
```

```
                                -continued
GCC TTC CTG GAG CTG GAG GGG GAG GTG TAC CTC GTG GCC CTG GGC GCG      3132

Ala Phe Leu Glu Leu Glu Gly Glu Val Tyr Leu Val Ala Leu Gly Ala
        850                 855                 860

GAA AAG CGG GGC ACG GTG GAG GAG GAC CTG GCC CGC CTG GCC TAC GAC      3180

Glu Lys Arg Gly Thr Val Glu Glu Asp Leu Ala Arg Leu Ala Tyr Asp
865                 870                 875                 880

GTG GAG CGG GCC GTG CAC CTC GCC CTC GAG GCC CTG GAG GCG GAG CTT      3228

Val Glu Arg Ala Val His Leu Ala Leu Glu Ala Leu Glu Ala Glu Leu
                885                 890                 895

TGG GCC TTT GCC GAG GAG GTG GCC GAC CAC CTC CAC GCC GCC TTC CTC      3276

Trp Ala Phe Ala Glu Glu Val Ala Asp His Leu His Ala Ala Phe Leu
            900                 905                 910

CAA GCC TAC CGC TCC GCC CTC CCC GAG GAG GCC CTG GAG GAG GCG GGC      3324

Gln Ala Tyr Arg Ser Ala Leu Pro Glu Glu Ala Leu Glu Glu Ala Gly
                915                 920                 925

TGG ACG CGG CAC ATG GCC GAG GTG GCG GCG GAG CAC CTC CAC CGG GAG      3372

Trp Thr Arg His Met Ala Glu Val Ala Ala Glu His Leu His Arg Glu
        930                 935                 940

GAA AGG CCC GCC CGC AAG CGC ATC CAC GAG CGC TGG CAG GCC AAG GCC      3420

Glu Arg Pro Ala Arg Lys Arg Ile His Glu Arg Trp Gln Ala Lys Ala
945                 950                 955                 960

GGA AAA GCC                                                          3429

Gly Lys Ala
        963

TAGGCGCCCG GTAGCCCTTC AGCCCCGGGC CACGGGGCC TTGGGGTGGA AGACGGCCTC    3489

CTCGGGGAGG AGGCGGCGCT TCTTGGCCCG GCGGTAGACG GCGTCCCACA TGCGGCAGAA    3549

GGCGCACACC GCCCCCGTGG TGGGGTAGCC GCACCGCTCG CACTCCCTAA G             3600
```

As is described above, the present thermostable enzyme capable of converting maltose into trehalose and vice versa which was found as a result of the present inventors' long-term research, and, unlike conventional enzymes, the enzyme has a specific physicochemical properties. The present invention aims to prepare a recombinant enzyme by means of recombinant DNA technology. Referring the following examples, the process for preparing such a recombinant enzyme, its preparation and uses will be described in detail.

The recombinant enzyme as referred to in the present invention includes those in general which are prepared by recombinant DNA technology and capable of converting maltose into trehalose and vice versa. Usually the present recombinant DNA has a revealed amino acid sequence, e.g. the amino acid sequence in SEQ ID NO:3 or a homologous amino acid to it. Variants containing amino acid sequences, which are homologous to the amino acid sequence in SEQ ID NO:3, can be prepared by replacing one or more amino acids in SEQ ID NO:3 with other amino acids without alteriting the inherent activity of the enzyme. Although even when used the same DNA and it also depends on hosts into which the DNA is introduced, as well as on ingredients and components of nutrient culture media used for culturing transformants, and their cultivation temperature and pH, there may be produced modified enzymes which have the enzymatic activity inherent to the enzyme encoded by the DNA but lack one or more amino acids located near to the N-and/or the C-termini of the amino acid sequence in SEQ ID NO:3, or have one or more amino acids newly added to the N-terminus by the modification of intracellular enzymes of hosts after the DNA expression. Such variants can be included in the present recombinant enzyme as long as they have the desired properties.

The recombinant enzyme according to the present invention can be obtained from cultures of transformants containing the specific DNA. Transformants usable in the present invention can be obtained by introducing into appropriate hosts the base sequence in SEQ ID NO:4, homologous base sequences to it, or complementary base sequences to these base sequences. One or more bases in the above mentioned base sequences may be replaced with other bases by means of the degeneracy of genetic code without alteriting the amino acid sequence for which they code. Needless to say, one or more bases in the base sequence, which encodes the enzyme or their variants, can be readily replaced with other bases to allow the DNA to actually express the enzyme production in hosts.

Any DNA derived from natural resources and those artificially synthesized can be used in the present invention as long as they have the aforementioned base sequences. The natural resources of the DNA according to the present invention are, for example, microorganisms of the genus *Thermus aquaticus* (ATCC 33923) from which a gene, containing the DNA used in the present invention, can be obtained. These microorganisms can be inoculated into nutrient culture media and cultured for about 1–3 days under aerobic conditions, and the resultant cells were collected from cultures and subjected to ultrasonication or treated with a cell-wall lysis enzyme such as lysozyme or β-glucanase to extract genes containing the present DNA. In this case, a proteolytic enzyme such as protease can be used in combination with the cell-wall lysis enzyme, and, in the case of treating the cells with ultrasonication, they may be treated in the presence of a surfactant such as sodium dodecyl sulfate (SDS) or treated with the freezing and thawing method. The objective DNA is obtainable by treating the resultant with phenol extraction, alcohol sedimentation, centrifugation, protease treatment and/or ribonuclease treatment used in general in this field. To artificially synthesize the DNA according to the present invention, it can be chemically synthesized by using the base sequence in SEQ ID NO:3, or can be obtained in plasmid form by inserting a DNA, which encodes the amino acid sequence in SEQ ID NO:4, into an appropriate self-replicable vector to obtain a recombinant DNA, introducing the recombinant DNA into an appropriate host to obtain a transformant, culturing the transformant, separating the proliferated cells from the resultant culture, and collecting plasmids containing the recombinant DNA from the cells.

Such a recombinant DNA, for example, in the form of a recombinant DNA, is usually introduced into hosts. Generally the recombinant DNA contains the aforesaid DNA and a self-replicable vector and can be prepared by conventional method with a relative easiness when the material DNA is in hand. Examples of such a vector are plasmid vectors such as pBR322, pUC18, Bluescript II SK(+), pKK223-3, pUB110, pTZ4, pC194, pHV14, TRp7, TEp7, pBS7, etc.; and phage vectors such as λgt.λC, λgt.λB, ρ11, φ1, φ105, etc. Among these plasmid- and phage-vectors, pBR322, pUC18, Bluescript II SK(+), pKK223-3, λgt.λC and λgt.λB are satisfactorily used in case that the present DNA should be expressed in *Escherichia coli*, while pUB110, pTZ4, pC194, ρ11, φ1 and φ105 are satisfactorily used to express the DNA in microorganisms of the genus Bacillus. The plasmid vectors pHV14, TRp7, TEp7 and pBS7 are suitably used when the recombinant DNA is allowed to grow in 2 or more types of hosts.

The methods used to insert the present DNA into such vectors in the present invention may be conventional ones generally used in this field. A gene containing the present DNA and a self-replicable vector are first digested by a restriction enzyme and/or ultrasonic disintegrator, then the resultant DNA fragments and vector fragments are ligated. To ligate DNA fragments and vectors, they may be annealed if necessary, then subjected to the action of a DNA ligase in vivo or in vitro. The recombinant DNA thus obtained is replicable without substantial limitation by introducing it into an appropriate host, and culturing the resultant transformant.

The recombinant DNA according to the present invention can be introduced into appropriate host microorganisms including *Escherichia coli* and those of the genus Bacillus as well as actinomyces and yeasts. In the case of using *Escherichia coli* as a host, it can be cultured in the presence of the recombinant DNA and calcium ion, while in the case of using the microorganisms of the genus Bacillus the competent cell method and the colony hybridization method can be employed. Desired transformants can be cloned by the colony hybridization method or by culturing a variety of transformants in nutrient culture media containing either maltose or trehalose and selecting transformants which form trehalose or maltose.

The transformants thus obtained extracellularly produce the objective enzyme when cultured in nutrient culture media. Generally, liquid media in general supplemented with carbon sources, nitrogen sources and/or minerals, and, if necessary, further supplemented with a small amount of amino acids and/or vitamins can be used as the nutrient culture media. Examples of the carbon sources are saccharides such as starch, starch hydrolysate, glucose, fructose and sucrose. Examples of the nitrogen sources are organic- and inorganic-substances containing nitrogen such as ammonia, ammonium salts, urea, nitrate, peptone, yeast extract, defatted soy been, corn steep liquor and beef extract. Cultures containing the objective enzyme can be obtained by inoculating the transformants into nutrient culture media, and incubating them at a temperature of 20–50° C. and a pH of 2–9 for about 1–6 days under aerobic conditions by aeration-agitation, etc. Such cultures can be used intact as a crude enzyme preparation, and, usually, cells in the cultures can be disrupted with ultrasonic disintegrator and/or cell-wall lysis enzymes prior to use, followed by separating the enzyme from intact cells and cell debris by filtration and/or centrifugation, and purifying the enzyme. The methods used for purifying the enzyme in the invention include conventional ones in general. From cultures intact cells and cell debris are removed and subjected to one or more methods such as concentration, salting out, dialysis, separately sedimentation, gel filtration chromatography, ion-exchange chromatography, hydrophobic chromatography, affinity chromatography, gel electrophoresis and isoelectrophoresis.

As is described above, the present recombinant thermostable enzyme exerts a distinct activity of forming trehalose or maltose from maltose or trehalose respectively even when allowed to act at a temperature of over 55° C., and such an activity has not been found in conventional enzymes. Trehalose has a mild and high-quality sweetness and it has a great advantage of being capable of sweetening food products without fear of causing unsatisfactorily coloration and deterioration because it has no reducing residue within the molecule. By using these properties of the present recombinant thermostable enzyme, maltose, which could not have been used in some field due to its reducibility, can be converted into useful trehalose with a satisfactory handleability and substantial no reducibility.

Explaining now the present enzymatic conversion method in more detail, the wording "maltose" as referred to in the present invention usually means a saccharide composition containing maltose, and any material or method can be used in the present invention as long as trehalose is formed when the present recombinant thermostable enzyme acts thereon or formed thereby. To effectively produce trehalose in an industrial scale, saccharide compositions with a relatively-high maltose content, i.e., usually, about 70 w/w % or more, preferably, about 80 w/w % or more, can be arbitrarily used. Such saccharide compositions can be prepared by conventional methods generally used in this field, for example, those as disclosed in Japanese Patent Publication Nos.11,437/81 and 17,078/81 wherein β-amylase is allowed to act on gelatinized- or liquefied-starch and separating the formed maltose by separation-sedimentation method or dialysis method, or those as disclosed in Japanese Patent Publication Nos.13,089/72 and 3,938/79 wherein β-amylase is allowed to act on gelatinized- or liquefied-starch together with a starch debranching enzyme such as isoamylase or pullulanase.

In the enzymatic conversion method according to the present invention, an effective amount of the present recombinant thermostable enzyme is allowed to coexist in an aqueous medium containing maltose, followed by keeping the resultant mixture at a prescribed temperature and pH to enzymatically react until the desired amount of trehalose is formed. Although the enzymatic reaction proceeds even at a relatively-low concentration of about 0.1 w/w %, d.s.b., the concentration may be set to about 2 w/w % or more, d.s.b., preferably, about 5–50 w/w %, d.s.b., to proceed the enzymatic conversion method in an industrial scale. The reaction temperature and pH are set within the range which effectively forms maltose without inactivating the recombinant enzyme, i.e. a temperature of over 55° C., preferably, about 56–63° C., and a pH of about 5–10, preferably, about 6–7. The amount of the recombinant enzyme and the reaction time are appropriately set depending on the conditions of the enzymatic reaction. The present enzymatic conversion method effectively converts maltose into trehalose, and the conversion rate reaches up to about 50% or more in some cases.

The reaction mixtures obtainable by the present enzymatic conversion method can be used intact, and, usually, they may be purified prior to use. For example, the reaction mixtures are filtered and centrifuged to remove insoluble substances, and the resultant solutions are decolored with an activated charcoal, desalted and purified with an ion-exchange resin, and concentrated into syrupy products. Depending on use, the syrupy products can be dried in vacuo and spray-dried into solid products. To obtain products substantially consisting of trehalose, the syrupy products are subjected to one or more methods of chromatographies using ion exchangers, activated charcoals or silica gels, fermentation using yeasts, and removal by decomposing reducing saccharides with alkalis. To treat a relatively-large amount of reaction mixtures, ion-exchange chromatographies such as fixed bed-, moving bed-, and pseudo-moving bed-methods as disclosed in Japanese Patent Laid-Open Nos.23,799/83 and 72,598/83 are arbitrarily used in the invention, and these enable the effective and large production of high-trehalose content products which have been difficult to obtain in large quantities.

The trehalose and saccharide compositions containing trehalose thus obtained can be used in a variety of products which should be avoided from the reducibility of saccharide sweeteners, and therefore, they can be arbitrarily used in food products in general, cosmetics and pharmaceuticals as a sweetener, taste-improving agent, quality-improving agent, stability, filler, adjuvant or excipient.

The following examples explain the preparation of the recombinant thermostable enzyme and the enzymatic conversion method of maltose according to the present invention:

Example A-1
Preparation of Recombinant Enzyme

To 500-ml Erlenmeyer flasks were added 100 ml aliquots of a nutrient culture medium consisting of 2.0 w/v % glucose, 0.5 w/v % peptone, 0.1 w/v % yeast extract, 0.1 w/v % dipotassium hydrogen phosphate, 0.06 w/v % sodium dihydrogen phosphate, 0.05 w/v % magnesium sulfate heptahydrate, 0.5 w/v % calcium carbonate and water, and each flask was sterilized by heating at 115° C. for 30 min, cooled, admixed with 50 µg/ml ampicillin, and inoculated with the transformant BTM22 obtained in Experiment 1-2, followed by the incubation at 37° C. for 24 hours under rotatory-shaking conditions to obtain a seed culture. To 30-L jar fermenters were added 18 L aliquots of a fresh preparation of the same nutrient culture medium, sterilized similarly as above, admixed with 50 µg/ml ampicillin, and inoculated with 1 v/v % of the seed culture, followed by the incubation at 37° C. and a pH of 6–8 for 24 hours under aeration-agitation conditions. The resultant cultures were pooled, treated with ultrasonication to disrupt cells, centrifuged to remove insoluble substances, followed by assaying the enzymatic activity of the resultant supernatant. As a result, one L of the culture contained about 800 units of the recombinant enzyme. The assay of the supernatant conducted by the method in Experiment 1-1 revealed that in this culture was obtained an about 5 ml aqueous solution containing about 152 units/ml of a recombinant enzyme with a specific activity of about 135 units/mg protein.

Example A-2
Preparation of Recombinant Thermostable Enzyme

Example A-2(a)
Preparation of Transformant BTM23

Recombinant DNA pBTM22, obtained by the method in Example 3-2, was cleaved with Hind III, a restriction enzyme, to obtain a DNA fragment consisting of about 8,100 base pairs which contain the base sequence positioning from 107 to 2,889 in SEQ ID NO:4.

Eight oligonucleotides containing base sequences represented by

```
5'-AGCTTGAATTCTTTTTTAATAAAATCAGGAGGAAAAACCATGGACC-3',    (SEQ ID NO:10)

5'-CCCTCTGGTACAAGGACGCGGTGATCTACCAGCTCCAC-3',            (SEQ ID NO:11)

5'-GTCCGCTCCTTCTTTGACGCCAACAACGACGGCTACGG-3',            (SEQ ID NO:12)

5'-GGACTTTGAGGGCCTGAGGCGGA-3',                           (SEQ ID NO:13)

5'-AGCTTCCGCCTCAGGCCCTCAAAGTCCCCGTAGCCGTCGTTGTTG-3',    (SEQ ID NO:14)

5'-GCGTCAAAGAAGGAGCGGACGTGGAGCTGGTAGATCACC-3',           (SEQ ID NO:15)

5'-GCGTCCTTGTACCAGAGGGGGTCCATGGTTTTTCCTCC-3', and        (SEQ ID NO:16)

5'-TGATTTTATTAAAAAAGAATTCA-3                             (SEQ ID NO:17)
``` were mixed in adequate amounts, and the mixture was successively incubated at 100° C., 65° C., 37° C. and 20° C. for 20 min, respectively, to anneal the oligonucleotides. A first recombinant DNA, which contains the base sequence in SEQ ID NO:6 and a base sequence consisting of the bases of positions 1–2,889 in SEQ ID NO:3 wherein the guanines (G) located in the positions 1–963 were replaced with adenines (A), was obtained by adding the above DNA fragment to a double stranded DNA of 141 base pairs having 5' cohesive end of 4 bases at each terminus, which consists of the base sequence in SEQ ID NO:6 and the bases of positions 1–110 in SEQ ID NO:4 wherein the guanine (G) located in the position 1 in SEQ ID NO:4 was replaced with adenine (A) without alternating the amino acid sequence consisting of those of positions 1–36 in SEQ ID NO:3, and allowing the mixture to stand at 4° C. overnight in the presence of T4 DNA ligase to anneal the contents.

```
SEQ ID NO:6:
AGCTTGAATT CTTTTTTAAT AAAATCAGGA GGAAAAACC  39
```

Recombinant DNA pBTM22 obtained by the method in Experiment 3-2 was cleaved with Bam HI, a restriction enzyme, to obtain a DNA fragment consisting of about 2,400 base pairs which contains the base sequence positioning from 1,008 to 2,889 in SEQ ID NO:4 which was then ligated with "M13tv19 RF DNA", a phage vector commercialized by Takara Shuzo Co., Ltd., Tokyo, Japan, which had been cleaved with Bam HI to obtain a second recombinant DNA.

An oligonucleotide containing a base sequence represented by 5'-CGGTAGCCCTGCAGCCCCGGG-3' corresponding to the base sequence positioning at 3,438 to 3,458 in SEQ ID NO:5, where "thymine (T)", the base positioning at 3,448 in SEQ ID NO:5 was replaced with "guanine (G)", was in usual manner chemically synthesized. By using the synthesized oligonucleotide and "MUTAN-G", a site-specific mutation system commercialized by Takara Shuzo Co., Ltd., Tokyo, Japan, a third recombinant DNA, which contained the base sequence positioning from 1,008 to 2,889 bases in SEQ ID NO:4 where "thymine (T)", i.e. the base positioning at 3,448 in SEQ ID NO:5, was replaced with "guanine (G)" without alternating the amino acid sequence positioning from 337 to 963 bases in SEQ ID NO:5 which was contained in the second recombinant DNA, was obtained. The procedure of site-specific mutation followed the manual affixed to the "MUTAN-G".

A DNA fragment, consisting of about 1,390 base pairs containing the base sequence positioning at 1 to 1,358 bases in SEQ ID NO:4 where "guanine (G)", i.e. the first base in SEQ ID NO:4, was replaced with "adenine (A)", obtained by cleaving with restriction enzymes Eco RI and Bgl II, and a DNA fragment consisting of abut 1,550 base pairs containing the base sequence positioning at 1,359 to 2,889 in SEQ ID NO:4 obtained by cleaving the third recombinant DNA with restriction enzymes Bgl II and Pst I, were ligated to "pKK223-3", a plasmid vector commercialized by Pharmacia LKB Biotechnology AB, Uppsala, Sweden, with T4 DNA ligase to obtain the recombinant DNA pBTM23 containing the base sequence in SEQ ID NO:4.

Figure 6:
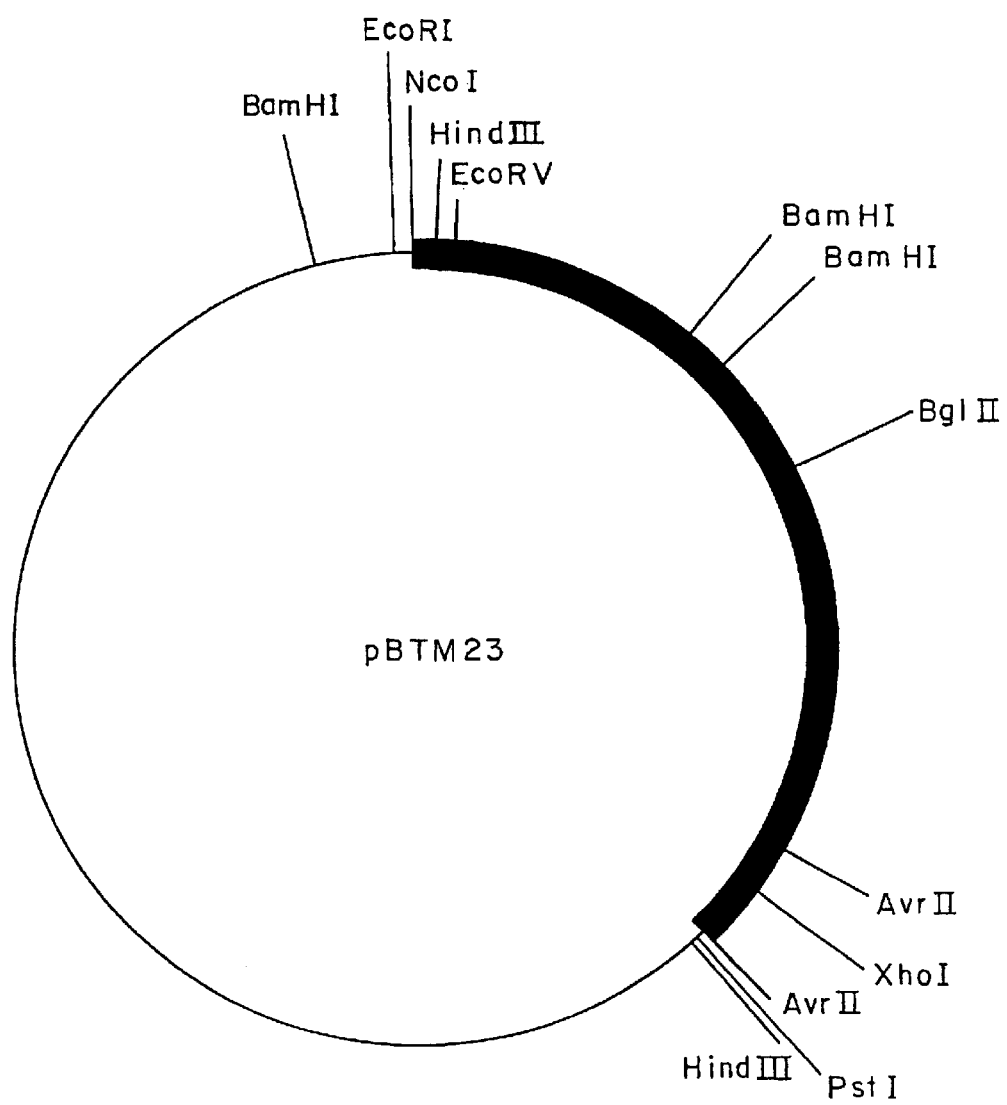
FIG. 6 shows the structure of the recombinant DNA pBTM23 according to the present invention.

The recombinant DNA pBTM23 thus obtained was introduced into *Escherichia coli* LE 392 (ATCC 33572) which had been previously prepared into a competent cell according to the method as described by J. Sambrook in *"Molecular Cloning, A Laboratory Manual"*, 2nd edition, pp.1.74–1.81 (1989), published by Cold Spring Harbor Laboratory Press, New York, USA, to obtain the present transformant BTM23 containing the DNA coding for the present enzyme. The transformant was cultured by the method in Experiment 3-2, and the proliferated cells were collected from the resultant culture, and lysed to extract the recombinant DNA which was then purified and analyzed, revealing that the recombinant DNA pBTM23 in FIG. 6 consisted of about 7,500 base pairs and had a DNA fragment containing 2,889 base pairs which was ligated to the downstream of Nco I, a restriction enzyme.

Example A-2(b)
Preparation of Recombinant Thermostable Enzyme using Transformant The transformant BTM23 was cultured similarly as in Example A-1 except that a liquid culture medium (pH 7.0) consisting of one w/v % maltose, 3 w/v % polypeptone, one w/v % "MEAST P1G", a product of Asahi Breweries, Ltd., Tokyo, Japan, 0.1 w/v % sodium dihydrogen phosphate dihydrate, 200 μg/ml ampicillin sodium and water was used. To the resultant culture were added lysozyme from albumen, commercialized by Seikagaku-Kogyo Co., Ltd., Tokyo, Japan, and "TRITON X-100", a surfactant to give respective concentrations of 0.1 mg/ml; and 1 mg/ml, and the resultant was incubated at 37° C. for 16 hours while stirring to extract a recombinant thermostable enzyme from the cells. The suspension was heated at 60° C. for one hour to inactivate concomitant enzymes from *Escherichia coli*, followed by centrifuging the mixture to remove impurities, and assaying the enzyme activity in the supernatant, revealing that one L culture contained about 120,000 units of the recombinant thermostable enzyme. The supernatant was purified by the method in Experiment 1 to obtain an about 177 ml aqueous solution containing about 1,400 units/ml of the recombinant thermostable enzyme with a specific activity of about 135 units/mg protein.

The properties and features of the purified enzyme were studied by the method Experiment 2, revealing that it has a molecular weight of 100,000–110,000 daltons on sodium dodecyl sulfate polyacrylamide gel electrophoresis (SDS-PAGE) and an isoelectric point of about 3.8–4.8 on isoelectrophoresis, and it is not inactivated even when incubated at 80° C. for 60 min in an aqueous solution (pH 7.0). These physicochemical properties are substantially the same of those of *Thermus aquaticus* (ATCC 33923) as a donor microorganism.

Example B-1
Preparation of Trehalose Syrup by Recombinant Enzyme

Potato starch powder was suspended in water to give a concentration of 10 w/w %, and the suspension was adjusted to pH 5.5, admixed with 2 units/g starch of "SPITASE HS", an α-amylase specimen commercialized by Nagase Biochemicals, Ltd., Kyoto, Japan, and heated at 95° C. to effect gelatinization and liquefaction. Thereafter, the resultant liquefied solution was autoclaved at 120° C. for 20 min to inactivate the remaining enzyme, promptly cooled to 50° C., adjusted to pH 5.0, admixed with 500 units/g starch of an isoamylase specimen commercialized by Hayashibara Biochemical Laboratories, Inc., Okayama, Japan, and 20 units/g starch of a β-amylase specimen commercialized by Nagase Biochemicals, Ltd., Kyoto, Japan, and subjected to an enzymatic reaction at 50° C. for 24 hours to obtain a saccharide solution containing about 92 w/w % maltose, d.s.b. The saccharide solution was heated at 100° C. for 20 min to inactivate the remaining enzyme, cooled to 60° C., adjusted to pH 6.5, admixed with one unit/g starch of the recombinant enzyme obtained in Example A-1, and subjected to an enzymatic reaction for 96 hours. The reaction mixture was heated at 100° C. for 10 min to inactivate the remaining enzyme, cooled, filtered, and, in usual manner, decolored with an activated charcoal, desalted and deionized with an ion-exchange resin, and concentrated to obtain a 70 w/w % syrup in a yield of about 95% to the material starch, d.s.b.

The product contains about 68 w/w % trehalose, d.s.b, and has a relatively-low reducibility because of its DE (dextrose equivalent) 18.4, as well as having a mild sweetness, moderate viscosity and moisture-retaining ability, and these render it arbitrarily useful in a variety of compositions such as food products, cosmetics and pharmaceuticals as a sweetener, taste-improving agent, stabilizer, filler, adjuvant or excipient.

Example B-2
Preparation of Trehalose Powder by Recombinant DNA

The reaction mixture obtained in Example B-1 was adjusted to pH 5.0, admixed with 10 units/g starch of "GLUCOZYME", a glucoamylase specimen commercialized by Nagase Biochemicals, Ltd., Kyoto, Japan, and subjected to an enzymatic reaction at 50° C. for 24 hours. The reaction mixture thus obtained was heated to inactivate the remaining enzyme, and, in usual manner, decolored, desalted, purified and subjected to ion-exchange column chromatography using "XT-1016 (polymerization degree of 4%)", a cation exchange resin in $Na^+$-form commercialized by Tokyo Organic Chemical Industries., Ltd., Tokyo, Japan, to increase the trehalose content. More particularly, the ion-exchange resin, previously suspended in water, was packed in 4 jacketed-stainless steel columns with an inner column diameter of 5.4 cm, and the columns were cascaded in series to give a total column length of 20 m. About 5 v/v % of the reaction mixture was fed to the columns while the inner column temperature was keeping at 60° C., and fractionated by feeding to the columns with 60° C. hot water at an SV (space velocity) 0.15, followed by collecting high-trehalose content fractions. The fractions were pooled, and, in usual manner, concentrated, dried in vacuo, and pulverized to obtain a trehalose powder in a yield of about 50% to the material, d.s.b.

The product, which contains about 97 w/w % trehalose, d.s.b, and has a relatively-low reducing power and a mild sweetness, can be arbitrarily incorporated into a variety of compositions such as food products, cosmetics and pharmaceuticals as a sweetener, taste-improving agent, stabilizer, filler, adjuvant or excipient.

Example B-3
Preparation of Crystalline Trehalose Powder by Recombinant Enzyme

A high-trehalose content fraction, obtained by the method in Example B-2, was in usual manner decolored with an activated charcoal, desalted with an ion-exchanger, and concentrated into an about 70 w/w % solution. The concentrate was placed in a crystallizer and gradually cooled while stirring to obtain a massecuite with a crystallization percentage of about 45%. The massecuite was sprayed at a pressure of about 150 $kg/cm^2$ from a nozzle equipped at the top of a drying tower while about 85° C. hot air was blowing downward from the top of the drying tower, about 45° C. hot air was blowing through under a wire-netting conveyer, which was equipped in the basement of the drying tower, to a crystalline powder collected on the conveyer, and the powder was gradually conveying out from the drying tower. Thereafter, the crystalline powder was transferred to an aging tower and aged for 10 hours in the stream of hot air to complete the crystallization and drying. Thus, a hydrous crystalline trehalose powder was obtained in a yield of about 90% to the material, d.s.b.

The product is substantially free from hygroscopicity and readily handleable, and it can be arbitrarily used in a variety compositions such as food products, cosmetics and pharmaceuticals as a sweetener, taste-improving agent, quality-improving agent, stability, filler, adjuvant or excipient.

Example B-4
Preparation of Anhydrous Crystalline Trehalose Powder by Recombinant Enzyme A high-trehalose content fraction, obtained by the method in Example B-2, was purified similarly as in Example B-3, and the resultant solution was transferred to a vessel and boiled under a reduced pressure to obtain a syrup with a moisture content of about 3.0 w/w %. The syrup was placed in a crystallizer, admixed with about 1.0 w/w % anhydrous crystalline trehalose as a seed crystal, crystallized at 120° C. while stirring, and transferred to a plain aluminum vessel, followed by aging the contents at 100° C. for 6 hours to form a block. The block thus obtained was pulverized with a cutter, dried by fluidized bed drying to obtain an anhydrous crystalline trehalose powder with a moisture content of about 0.3 w/w % in a yield of about 85% to the material, d.s.b.

The product with a strong dehydrating activity can be arbitrarily used as a desiccant for food products, cosmetics and pharmaceuticals, as well as their materials and intermediates, and also used as a white powdery sweetener with a mild sweetness in food products, cosmetics and pharmaceuticals.

Example B-5
Preparation of Trehalose Powder by Recombinant Enzyme

"MALTOSE HHH", a high-purity maltose commercialized by Hayashibara Biochemical Laboratories, Inc., Okayama, Japan, was dissolved in water to give a concentration of 40 w/w %, heated to 57° C., adjusted to pH 6.5, mixed with 2 units/g maltose, d.s.b., of a recombinant thermostable enzyme obtained by the method in Example A-2, followed by the enzymatic reaction for 48 hours. The reaction mixture was heated at 100° C. for 10 min to inactivate the remaining enzyme, cooled, filtered, decolored with an activated charcoal in usual manner, desalted and purified with an ion-exchange resin, dried in vacuo, and pulverized to obtain a powdery product containing about 73 w/w % trehalose, d.s.b., in a yield of about 90% to the material maltose, d.s.b.

Although the product has a DE (dextrose equivalent) of 19 which is about 30% of that of maltose, it has the same viscosity as that of maltose, as well as having a mild sweetness and an adequate moisture-retaining ability. Thus, the product can be arbitrarily used as a sweetener, quality-improving agent, stabilizer, filler, adjuvant and excipient in a variety of compositions such as food products, cosmetics and pharmaceuticals.

As is described above, the present invention is based on the finding of a novel thermostable enzyme which forms trehalose or maltose when acts on maltose or trehalose. The present invention aims to explore a way to produce such an enzyme in an industrial scale and in a considerably-high yield by recombinant DNA technology. The enzymatic conversion method using the present recombinant thermostable enzyme converts maltose into a saccharide composition containing trehalose, glucose and/or maltose in a considerably-high yield. Trehalose has a mild and high-quality sweetness, and does not have a reducing residue within the molecule, and because of these it can readily sweeten food products in general without fear of causing unsatisfactory coloration and deterioration. The recombinant enzyme with a revealed amino acid sequence can be used with a greater safety for the preparation of trehalose which is premised to be used in food products.

Therefore, the present invention is a useful invention which exerts the aforesaid significant action and effect as well as giving a great contribution to this field.

While there has been described what is at present considered to be the preferred embodiments of the invention, it will be understood the various modifications may be made therein, and it is intended to cover in the appended claims all such modifications as fall within the true spirit and scope of the invention.

We claim:

1. A recombinant enzyme which is capable of converting maltose into trehalose and which enzyme is stable up to a temperature of at least 55° C., said enzyme being prepared by introducing the expression of a DNA molecule comprising a nucleotide sequence selected from the group consisting of enzymatically active fragments of SEQ ID NO:4 and enzymatically active fragments which have bases replaced by the degeneracy of the genetic code, said nucleotide sequence containing bases 1–60 and 706–750 of SEQ ID NO:4 and encoding an enzyme having substantially the same enzyme activity as the enzyme of SEQ ID NO:3.

2. An enzymatic conversion method for preparing trehalose from maltose comprising contacting a reaction mixture containing maltose with the recombinant enzyme according to claim 1 to form trehalose.

3. The method according to claim 2 wherein said maltose is present in the reaction mixture in an amount up to 50 w/w % maltose, and conducting the conversion at a temperature of more than 55° C. and a pH of 5–10.

4. The method according to claim 2 wherein the reaction mixture contains at least about 50 w/w % trehalose, on a dry solid basis.

5. The recombinant enzyme of claim 1 which has an amino acid sequence selected from the group consisting of SEQ ID NO:3 obtained by replacing at least one amino acid in SEQ ID NO:3 with other amino acids without altering the inherent activity of the enzyme.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH:20 amino acids
      (B) TYPE:amino acid
      (C) STRANDEDNESS: single
      (D) TOPOLOGY:linear (ii) MOLECULE TYPE:peptide (xi) SEQUENCE DESCRIPTION:SEQ ID NO:1:

```
Met Asp Pro Leu Trp Tyr Lys Asp Ala Val Ile Tyr Gln Leu His Val
1               5                   10                  15

Arg Ser Phe Phe
        20
```

(2) INFORMATION FOR SEQ ID NO:2:

(i) SEQUENCE CHARACTERISTICS:
      (A) LENGTH:15 amino acids
      (B) TYPE:amino acid
      (C) STRANDEDNESS: single
      (D) TOPOLOGY:linear (ii) MOLECULE TYPE:peptide (xi) SEQUENCE DESCRIPTION:SEQ ID NO:2:

```
Ile Leu Leu Ala Glu Ala Asn Met Trp Pro Glu Glu Thr Leu Pro
1               5                   10                  15
```

(2) INFORMATION FOR SEQ ID NO:3:

(i) SEQUENCE CHARACTERISTICS:
      (A) LENGTH:963 amino acids
      (B) TYPE:amino acid
      (C) STRANDEDNESS: single
      (D) TOPOLOGY:linear (ii) MOLECULE TYPE:peptide (xi) SEQUENCE DESCRIPTION:SEQ ID NO:3:

```
Met Asp Pro Leu Trp Tyr Lys Asp Ala Val Ile Tyr Gln Leu His Val
1               5                   10                  15

Arg Ser Phe Phe Asp Ala Asn Asn Asp Gly Tyr Gly Asp Phe Glu Gly
            20                  25                  30

Leu Arg Arg Lys Leu Pro Tyr Leu Glu Glu Leu Gly Val Asn Thr Leu
        35                  40                  45

Trp Leu Met Pro Phe Phe Gln Ser Pro Leu Arg Asp Asp Gly Tyr Asp
    50                  55                  60

Ile Ser Asp Tyr Tyr Gln Ile Leu Pro Val His Gly Thr Leu Glu Asp
65                  70                  75                  80

Phe Thr Val Asp Glu Ala His Gly Arg Gly Met Lys Val Ile Ile Glu
                85                  90                  95

Leu Val Leu Asn His Thr Ser Ile Asp His Pro Trp Phe Gln Glu Ala
                100                 105                 110

Arg Lys Pro Asn Ser Pro Met Arg Asp Trp Tyr Val Trp Ser Asp Thr
            115                 120                 125
```

-continued

```
Pro Glu Lys Tyr Lys Gly Val Arg Val Ile Phe Lys Asp Phe Glu Thr
    130                 135                 140

Ser Asn Trp Thr Phe Asp Pro Val Ala Lys Ala Tyr Tyr Trp His Arg
145                 150                 155                 160

Phe Tyr Trp His Gln Pro Asp Leu Asn Trp Asp Ser Pro Glu Val Glu
                165                 170                 175

Lys Ala Ile His Gln Val Met Phe Phe Trp Ala Asp Leu Gly Val Asp
                180                 185                 190

Gly Phe Arg Leu Asp Ala Ile Pro Tyr Leu Tyr Glu Arg Glu Gly Thr
            195                 200                 205

Ser Cys Glu Asn Leu Pro Glu Thr Ile Glu Ala Val Lys Arg Leu Arg
210                 215                 220

Lys Ala Leu Glu Glu Arg Tyr Gly Pro Gly Lys Ile Leu Leu Ala Glu
225                 230                 235                 240

Ala Asn Met Trp Pro Glu Glu Thr Leu Pro Tyr Phe Gly Asp Gly Asp
                245                 250                 255

Gly Val His Met Ala Tyr Asn Phe Pro Leu Met Pro Arg Ile Phe Met
            260                 265                 270

Ala Leu Arg Arg Glu Asp Arg Gly Pro Ile Glu Thr Met Leu Lys Glu
            275                 280                 285

Ala Glu Gly Ile Pro Glu Thr Ala Gln Trp Ala Leu Phe Leu Arg Asn
290                 295                 300

His Asp Glu Leu Thr Leu Glu Lys Val Thr Glu Glu Arg Glu Phe
305                 310                 315                 320

Met Tyr Glu Ala Tyr Ala Pro Asp Pro Lys Phe Arg Ile Asn Leu Gly
                325                 330                 335

Ile Arg Arg Arg Leu Met Pro Leu Leu Gly Gly Asp Arg Arg Arg Tyr
            340                 345                 350

Glu Leu Leu Thr Ala Leu Leu Leu Thr Leu Lys Gly Thr Pro Ile Val
            355                 360                 365

Tyr Tyr Gly Asp Glu Ile Gly Met Gly Asp Asn Pro Phe Leu Gly Asp
    370                 375                 380

Arg Asn Gly Val Arg Thr Pro Met Gln Trp Ser Gln Asp Arg Ile Val
385                 390                 395                 400

Ala Phe Ser Arg Ala Pro Tyr His Ala Leu Phe Leu Pro Pro Val Ser
                405                 410                 415

Glu Gly Pro Tyr Ser Tyr His Phe Val Asn Val Glu Ala Gln Arg Glu
                420                 425                 430

Asn Pro His Ser Leu Leu Ser Phe Asn Arg Arg Phe Leu Ala Leu Arg
            435                 440                 445

Asn Gln His Ala Lys Ile Phe Gly Arg Gly Ser Leu Thr Leu Leu Pro
            450                 455                 460

Val Glu Asn Arg Arg Val Leu Ala Tyr Leu Arg Glu His Glu Gly Glu
465                 470                 475                 480

Arg Val Leu Val Val Ala Asn Leu Ser Arg Tyr Thr Gln Ala Phe Asp
                485                 490                 495

Leu Pro Leu Glu Ala Tyr Gln Gly Leu Val Pro Val Glu Leu Phe Ser
            500                 505                 510

Gln Gln Pro Phe Pro Pro Val Glu Gly Arg Tyr Arg Leu Thr Leu Gly
            515                 520                 525

Pro His Gly Phe Ala Leu Phe Ala Leu Lys Pro Val Glu Ala Val Leu
    530                 535                 540

His Leu Pro Ser Pro Asp Trp Ala Glu Glu Pro Ala Pro Glu Glu Ala
```

```
              545                 550                 555                 560
        Asp Leu Pro Arg Val His Met Pro Gly Gly Pro Glu Val Leu Leu Val
                        565                 570                 575

Asp Thr Leu Val His Glu Arg Gly Arg Glu Leu Leu Asn Ala Leu
                        580                 585                 590

Ala Gln Thr Leu Lys Glu Lys Ser Trp Leu Ala Leu Lys Pro Gln Lys
                        595                 600                 605

Val Ala Leu Leu Asp Ala Leu Arg Phe Gln Lys Asp Pro Pro Leu Tyr
                    610                 615                 620

Leu Thr Leu Leu Gln Leu Glu Asn His Arg Thr Leu Gln Val Ser Leu
        625                 630                 635                 640

Pro Leu Leu Trp Ser Pro Gln Arg Arg Glu Gly Pro Gly Leu Phe Ala
                            645                 650                 655

Arg Thr His Gly Gln Pro Gly Tyr Phe Tyr Glu Leu Ser Leu Asp Pro
                        660                 665                 670

Gly Phe Tyr Arg Leu Leu Ala Arg Leu Lys Glu Gly Phe Glu Gly
                    675                 680                 685

Arg Ser Leu Arg Ala Tyr Tyr Arg Gly Arg His Pro Gly Pro Val Pro
                690                 695                 700

Glu Ala Val Asp Leu Leu Arg Pro Gly Leu Ala Ala Gly Glu Gly Val
        705                 710                 715                 720

Trp Val Gln Leu Gly Leu Val Gln Asp Gly Gly Leu Asp Arg Thr Glu
                            725                 730                 735

Arg Val Leu Pro Arg Leu Asp Leu Pro Trp Val Leu Arg Pro Glu Gly
                        740                 745                 750

Gly Leu Phe Trp Glu Arg Gly Ala Ser Arg Arg Val Leu Ala Leu Thr
                    755                 760                 765

Gly Ser Leu Pro Pro Gly Arg Pro Gln Asp Leu Phe Ala Ala Leu Glu
                770                 775                 780

Val Arg Leu Leu Glu Ser Leu Pro Arg Leu Arg Gly His Ala Pro Gly
        785                 790                 795                 800

Thr Pro Gly Leu Leu Pro Gly Ala Leu His Glu Thr Glu Ala Leu Val
                            805                 810                 815

Arg Leu Leu Gly Val Arg Leu Ala Leu Leu His Arg Ala Leu Gly Glu
                        820                 825                 830

Val Glu Gly Val Val Gly Gly His Pro Leu Leu Gly Arg Gly Leu Gly
                    835                 840                 845

Ala Phe Leu Glu Leu Glu Gly Glu Val Tyr Leu Val Ala Leu Gly Ala
                850                 855                 860

Glu Lys Arg Gly Thr Val Glu Glu Asp Leu Ala Arg Leu Ala Tyr Asp
        865                 870                 875                 880

Val Glu Arg Ala Val His Leu Ala Leu Glu Ala Leu Glu Ala Glu Leu
                            885                 890                 895

Trp Ala Phe Ala Glu Glu Val Ala Asp His Leu His Ala Ala Phe Leu
                        900                 905                 910

Gln Ala Tyr Arg Ser Ala Leu Pro Glu Glu Ala Leu Glu Glu Ala Gly
                    915                 920                 925

Trp Thr Arg His Met Ala Glu Val Ala Ala Glu His Leu His Arg Glu
                930                 935                 940

Glu Arg Pro Ala Arg Lys Arg Ile His Glu Arg Trp Gln Ala Lys Ala
        945                 950                 955                 960

Gly Lys Ala
```

(2) INFORMATION FOR SEQ ID NO:4:

(i) SEQUENCE CHARACTERISTICS:
        (A) LENGTH:2889 base pairs
        (B) TYPE:nucleic acid
        (C) STRANDEDNESS: single
        (D) TOPOLOGY:linear (ii) MOLECULE TYPE: cDNA (xi) SEQUENCE DESCRIPTION:SEQ ID NO:4:

```
GTGGACCCCC TCTGGTACAA GGACGCGGTG ATCTACCAGC TCCACGTCCG CTCCTTCTTT      60

GACGCCAACA ACGACGGCTA CGGGGACTTT GAGGGCCTGA GGCGGAAGCT TCCCTACCTG     120

GAGGAGCTCG GGGTCAACAC CCTCTGGCTC ATGCCCTTCT TCCAGTCCCC CTTGAGGGAC     180

GACGGGTACG ATATCTCCGA CTACTACCAG ATCCTCCCCG TCCACGGGAC CCTGGAGGAC     240

TTCACCGTGG ACGAGGCCCA CGGCCGGGGG ATGAAGGTGA TCATTGAGCT CGTCCTGAAC     300

CACACCTCCA TTGACCACCC TTGGTTCCAG GAGGCGAGGA AGCCGAATAG CCCCATGCGG     360

GACTGGTACG TGTGGAGCGA CACCCCGGAG AAGTACAAGG GGGTCCGGGT CATCTTCAAG     420

GACTTTGAAA CCTCCAACTG GACCTTTGAC CCCGTGGCCA AGGCCTACTA CTGGCACCGC     480

TTCTACTGGC ACCAGCCCGA CCTCAACTGG GACAGCCCCG AGGTGGAGAA GGCCATCCAC     540

CAGGTCATGT TCTTCTGGGC CGACCTGGGG GTGGACGGCT TCCGCCTGGA CGCCATCCCC     600

TACCTCTACG AGCGGGAGGG GACCTCCTGC GAGAACCTCC CCGAGACCAT TGAGGCGGTG     660

AAGCGCCTGA GGAAGGCCCT GGAGGAGCGC TACGCCCCCG GAAGATCCT CCTCGCCGAG     720

GCCAACATGT GGCGGAGGA GACCCTCCCC TACTTCGGGG ACGGGACGG GGTCCACATG     780

GCCTACAACT TCCCCCTGAT GCCCCGGATC TTCATGGCCC TAAGGCGGGA GGACCGGGGT     840

CCCATTGAAA CCATGCTCAA GGAGGCGGAG GGGATCCCCG AAACCGCCCA GTGGGCCCTC     900

TTCCTCCGCA ACCACGACGA GCTCACCCTG GAGAAGGTCA CGGAGGAGGA GCGGGAGTTC     960

ATGTACGAGG CCTACGCCCC CGACCCCAAG TTCCGCATCA ACCTGGGGAT CCGCCGCCGC    1020

CTCATGCCCC TCCTCGGGGG CGACCGCAGG CGGTACGAGC TCCTCACCGC CCTCCTCCTC    1080

ACCCTAAAGG GCACGCCCAT CGTCTACTAC GGGGACGAGA TCGGCATGGG GGACAACCCC    1140

TTCCTCGGGG ACCGGAACGG TGTCAGGACC CCCATGCAGT GGTCCCAAGA CCGCATCGTC    1200

GCCTTCTCCC GCGCCCCCTA CCACGCCCTC TTCCTTCCCC CCGTGAGCGA GGGGCCCTAC    1260

AGCTACCACT TCGTCAACGT GGAGGCCCAG CGGGAAAACC CCCACTCCCT CCTGAGCTTC    1320

AACCGCCGCT TCCTCGCCCT GAGGAACCAG CACGCCAAGA TCTTCGGCCG GGGGAGCCTC    1380

ACCCTTCTCC CCGTGGAGAA CCGGCGCGTC CTCGCCTACC TGAGGGAGCA CGAGGGGGAG    1440

CGGGTCCTGG TGGTGGCCAA CCTCTCCCGC TACACCCAGG CCTTTGACCT CCCCTTGGAG    1500

GCCTACCAAG GCCTCGTCCC CGTGGAGCTC TTCTCGCAGC AACCCTTCCC CCCGGTGGAG    1560

GGGCGCTACC GCTTGACCCT GGGCCCCCAC GGCTTCGCCC TCTTCGCCCT GAAGCCCGTG    1620

GAGGCGGTGC TCCACCTCCC CTCCCCCGAC TGGGCCGAGG AGCCCGCCCC CGAGGAGGCC    1680

GACCTGCCCC GGGTCCACAT GCCCGGGGGG CCGGAGGTCC TCCTGGTGGA CACCCTGGTC    1740

CACGAAAGGG GGCGGAGGA GCTCCTAAAC GCCCTCGCCC AGACCCTGAA GGAGAAGAGC    1800

TGGCTCGCCC TCAAGCCGCA GAAGGTGGCC CTCCTGGACG CCCTCCGCTT CCAGAAGGAC    1860

CCGCCCCTTT ACCTCACCCT GCTCCAGCTG GAGAACCACA GGACCCTCCA GGTCTCCCTC    1920

CCCCTCCTCT GGTCCCCCCA GAGGCGGGAA GGCCCCGGCC TCTTCGCCCG CACCCACGGC    1980
```

-continued

```
CAGCCCGGCT ACTTCTACGA GCTCTCCTTG GACCCAGGCT TCTACCGCCT CCTCCTCGCC    2040

CGCCTTAAGG AGGGGTTTGA GGGGCGGAGC CTCCGGGCCT ACTACCGCGG CCGCCACCCG    2100

GGTCCCGTGC CCGAGGCCGT GGACCTCCTC CGGCCGGGAC TCGCGGCGGG GGAGGGGGTC    2160

TGGGTCCAGC TCGGCCTCGT CCAAGACGGG GGCCTGGACC GCACGGAGCG GGTCCTCCCC    2220

CGCCTGGACC TCCCCTGGGT TCTCCGGCCC GAAGGGGGCC TCTTCTGGGA GCGGGGCGCC    2280

TCCAGAAGGG TCCTCGCCCT CACGGGAAGC CTCCCCCCGG GCCGCCCCCA GGACCTCTTC    2340

GCCGCCCTGG AGGTCCGGCT CCTGGAAAGC CTTCCCCGCC TCCGGGGGCA CGCCCCCGGG    2400

ACCCCAGGCC TCCTTCCCGG GGCCCTGCAC GAGACCGAAG CCCTGGTCCG CCTCCTCGGG    2460

GTGCGCCTCG CCCTCCTCCA CCGGGCCCTT GGGGAGGTGG AGGGGGTGGT GGGGGGCCAC    2520

CCCCTCCTAG GCCGCGGCCT CGGGGCCTTC CTGGAGCTGG AGGGGGAGGT GTACCTCGTG    2580

GCCCTGGGCG CGGAAAAGCG GGGCACGGTG GAGGAGGACC TGGCCCGCCT GGCCTACGAC    2640

GTGGAGCGGG CCGTGCACCT CGCCCTCGAG GCCCTGGAGG CGGAGCTTTG GCCCTTTGCC    2700

GAGGAGGTGG CCGACCACCT CCACGCCGCC TTCCTCCAAG CCTACCGCTC CGCCCTCCCC    2760

GAGGAGGCCC TGGAGGAGGC GGGCTGGACG CGGCACATGG CCGAGGTGGC GGCGGAGCAC    2820

CTCCACCGGG AGGAAAGGCC CGCCCGCAAG CGCATCCACG AGCGCTGGCA GGCCAAGGCC    2880

GGAAAAGCC                                                           2889
```

(2) INFORMATION FOR SEQ ID NO:5:

(i) SEQUENCE CHARACTERISTICS:
        (A) LENGTH:3600 base pairs
        (B) TYPE:nucleic acid
        (C) STRANDEDNESS:DOUBLE
        (D) TOPOLOGY:linear (ii) MOLECULE TYPE:genomic DNA (vi) ORIGINAL SOURCE:
        (A) ORGANISM:Thermus aquaticus
        (B) INDIVIDUAL ISOLATE:ATCC 33923

(ix) FEATURE:
        (A) NAME/KEY:5'UTR
        (B) LOCATION:1..540
        (C) IDENTIFICATION METHOD:E
        (A) NAME/KEY:mat peptide
        (B) LOCATION:541..3429
        (C) IDENTIFICATION METHOD:S
        (A) NAME/KEY:3'UTR
        (B) LOCATION:3430..3600
        (C) IDENTIFICATION METHOD:E (xi) SEQUENCE DESCRIPTION:SEQ ID NO:5:

```
GCCCCTCCCT CCCCCAACCG GGCCTTCCCG TGGGGGGGGG GCACAGCCTG GAGGAAGGGG     60

TGCTCGACGG GGAGGTGCGG CCCCTCTTGC GCCGTGGGCG GTGACCCCTT GCGGGCCAGG    120

CTTCCCTCCT ACCCCGGGGT GCGGGTGGAG GACAAGGGCT TCGCCCTGGC CCTGCACTAC    180

CGGGGGGCGA AGGGCGAGGA GAAGGCCCGG GCCTGCCTCG AGGCCTGGCT TAAGGCGGTG    240

GAGGGGCTCC TGGGGGCCTT GGGCCTCGAG GCCCTCCCCG GCAAGAGGGT CCTGGAGCTC    300

AAGCCCAAGG GGGTGGACAA GGGCCAAGCG GTCCTCAGGC TCCTCGGACG CCACCCGGAC    360

CACACCCCCG TTTACATCGG GGACGACACC ACCGACGAGG CCGCCTTCCT CGCCTTAAGG    420

GGCCGGGGCC TCACCTTCAA GGTGGGGGAA GGCCCACGG CGGCCCAAGG CCGGCTCAAG     480

GACGTGGAGG AGGTCCTGGC CTACTTGCAA ACCTACCTCG GACCCACTAG CCTTTAGGCC    540

GTG GAC CCC CTC TGG TAC AAG GAC GCG GTG ATC TAC CAG CTC CAC GTC      588
```

```
Met Asp Pro Leu Trp Tyr Lys Asp Ala Val Ile Tyr Gln Leu His Val
1               5                   10                  15

CGC TCC TTC TTT GAC GCC AAC AAC GAC GGC TAC GGG GAC TTT GAG GGC      636
Arg Ser Phe Phe Asp Ala Asn Asn Asp Gly Tyr Gly Asp Phe Glu Gly
20                  25                  30

CTG AGG CGG AAG CTT CCC TAC CTG GAG GAG CTC GGG GTC AAC ACC CTC      684
Leu Arg Arg Lys Leu Pro Tyr Leu Glu Glu Leu Gly Val Asn Thr Leu
35                  40                  45

TGG CTC ATG CCC TTC TTC CAG TCC CCC TTG AGG GAC GAC GGG TAC GAT      732
Trp Leu Met Pro Phe Phe Gln Ser Pro Leu Arg Asp Asp Gly Tyr Asp
50                  55                  60

ATC TCC GAC TAC TAC CAG ATC CTC CCC GTC CAC GGG ACC CTG GAG GAC      780
Ile Ser Asp Tyr Tyr Gln Ile Leu Pro Val His Gly Thr Leu Glu Asp
65                  70                  75                  80

TTC ACC GTG GAC GAG GCC CAC GGC CGG GGG ATG AAG GTG ATC ATT GAG      828
Phe Thr Val Asp Glu Ala His Gly Arg Gly Met Lys Val Ile Ile Glu
85                  90                  95

CTC GTC CTG AAC CAC ACC TCC ATT GAC CAC CCT TGG TTC CAG GAG GCG      876
Leu Val Leu Asn His Thr Ser Ile Asp His Pro Trp Phe Gln Glu Ala
100                 105                 110

AGG AAG CCG AAT AGC CCC ATG CGG GAC TGG TAC GTG TGG AGC GAC ACC      924
Arg Lys Pro Asn Ser Pro Met Arg Asp Trp Tyr Val Trp Ser Asp Thr
115                 120                 125

CCG GAG AAG TAC AAG GGG GTC CGG GTC ATC TTC AAG GAC TTT GAA ACC      972
Pro Glu Lys Tyr Lys Gly Val Arg Val Ile Phe Lys Asp Phe Glu Thr
130                 135                 140

TCC AAC TGG ACC TTT GAC CCC GTG GCC AAG GCC TAC TAC TGG CAC CGC     1020
Ser Asn Trp Thr Phe Asp Pro Val Ala Lys Ala Tyr Tyr Trp His Arg
145                 150                 155                 160

TTC TAC TGG CAC CAG CCC GAC CTC AAC TGG GAC AGC CCC GAG GTG GAG     1068
Phe Tyr Trp His Gln Pro Asp Leu Asn Trp Asp Ser Pro Glu Val Glu
165                 170                 175

AAG GCC ATC CAC CAG GTC ATG TTC TTC TGG GCC GAC CTG GGG GTG GAC     1116
Lys Ala Ile His Gln Val Met Phe Phe Trp Ala Asp Leu Gly Val Asp
180                 185                 190

GGC TTC CGC CTG GAC GCC ATC CCC TAC CTC TAC GAG CGG GAG GGG ACC     1164
Gly Phe Arg Leu Asp Ala Ile Pro Tyr Leu Tyr Glu Arg Glu Gly Thr
195                 200                 205

TCC TGC GAG AAC CTC CCC GAG ACC ATT GAG GCG GTG AAG CGC CTG AGG     1212
Ser Cys Glu Asn Leu Pro Glu Thr Ile Glu Ala Val Lys Arg Leu Arg
210                 215                 220

AAG GCC CTG GAG GAG CGC TAC GGC CCC GGG AAG ATC CTC CTC GCC GAG     1260
Lys Ala Leu Glu Glu Arg Tyr Gly Pro Gly Lys Ile Leu Leu Ala Glu
225                 230                 235                 240

GCC AAC ATG TGG CCG GAG GAG ACC CTC CCC TAC TTC GGG GAC GGG GAC     1308
Ala Asn Met Trp Pro Glu Glu Thr Leu Pro Tyr Phe Gly Asp Gly Asp
245                 250                 255

GGG GTC CAC ATG GCC TAC AAC TTC CCC CTG ATG CCC CGG ATC TTC ATG     1356
Gly Val His Met Ala Tyr Asn Phe Pro Leu Met Pro Arg Ile Phe Met
260                 265                 270

GCC CTA AGG CGG GAG GAC CGG GGT CCC ATT GAA ACC ATG CTC AAG GAG     1404
Ala Leu Arg Arg Glu Asp Arg Gly Pro Ile Glu Thr Met Leu Lys Glu
275                 280                 285

GCG GAG GGG ATC CCC GAA ACC GCC CAG TGG GCC CTC TTC CTC CGC AAC     1452
Ala Glu Gly Ile Pro Glu Thr Ala Gln Trp Ala Leu Phe Leu Arg Asn
290                 295                 300

CAC GAC GAG CTC ACC CTG GAG AAG GTC ACG GAG GAG GAG CGG GAG TTC     1500
His Asp Glu Leu Thr Leu Glu Lys Val Thr Glu Glu Glu Arg Glu Phe
305                 310                 315                 320
```

```
ATG TAC GAG GCC TAC GCC CCC GAC CCC AAG TTC CGC ATC AAC CTG GGG         1548
Met Tyr Glu Ala Tyr Ala Pro Asp Pro Lys Phe Arg Ile Asn Leu Gly
325                 330                 335

ATC CGC CGC CGC CTC ATG CCC CTC CTC GGG GGC GAC CGC AGG CGG TAC         1596
Ile Arg Arg Arg Leu Met Pro Leu Leu Gly Gly Asp Arg Arg Arg Tyr
340                 345                 350

GAG CTC CTC ACC GCC CTC CTC CTC ACC CTA AAG GGC ACG CCC ATC GTC         1644
Glu Leu Leu Thr Ala Leu Leu Leu Thr Leu Lys Gly Thr Pro Ile Val
355                 360                 365

TAC TAC GGG GAC GAG ATC GGC ATG GGC GAC AAC CCC TTC CTC GGG GAC         1692
Tyr Tyr Gly Asp Glu Ile Gly Met Gly Asp Asn Pro Phe Leu Gly Asp
370                 375                 380

CGG AAC GGT GTC AGG ACC CCC ATG CAG TGG TCC CAA GAC CGC ATC GTC         1740
Arg Asn Gly Val Arg Thr Pro Met Gln Trp Ser Gln Asp Arg Ile Val
385                 390                 395                 400

GCC TTC TCC CGC GCC CCC TAC CAC GCC CTC TTC CTT CCC CCC GTG AGC         1788
Ala Phe Ser Arg Ala Pro Tyr His Ala Leu Phe Leu Pro Pro Val Ser
405                 410                 415

GAG GGG CCC TAC AGC TAC CAC TTC GTC AAC GTG GAG GCC CAG CGG GAA         1836
Glu Gly Pro Tyr Ser Tyr His Phe Val Asn Val Glu Ala Gln Arg Glu
420                 425                 430

AAC CCC CAC TCC CTC CTG AGC TTC AAC CGC CGC TTC CTC GCC CTG AGG         1884
Asn Phe His Ser Leu Leu Ser Phe Asn Arg Arg Phe Leu Ala Leu Arg
435                 440                 445

AAC CAG CAC GCC AAG ATC TTC GGC CGG GGG AGC CTC ACC CTT CTC CCC         1932
Asn Gln His Ala Lys Ile Phe Gly Arg Gly Ser Leu Thr Leu Leu Pro
450                 455                 460

GTG GAG AAC CGG CGC GTC CTC GCC TAC CTG AGG GAG CAC GAG GGG GAG         1980
Val Glu Asn Arg Arg Val Leu Ala Tyr Leu Arg Glu His Glu Gly Glu
465                 470                 475                 480

CGG GTC CTG GTG GTG GCC AAC CTC TCC CGC TAC ACC CAG GCC TTT GAC         2028
Arg Val Leu Val Val Ala Asn Leu Ser Arg Tyr Thr Gln Ala Phe Asp
485                 490                 495

CTC CCC TTG GAG GCC TAC CAA GGC CTC GTC CCC GTG GAG CTC TTC TCG         2076
Leu Pro Leu Glu Ala Tyr Gln Gly Leu Val Pro Val Glu Leu Phe Ser
500                 505                 510

CAG CAA CCC TTC CCC CCG GTG GAG GGG CGC TAC CGC TTG ACC CTG GGC         2124
Gln Gln Pro Phe Pro Pro Val Glu Gly Arg Tyr Arg Leu Thr Leu Gly
515                 520                 525

CCC CAC GGC TTC GCC CTC TTC GCC CTG AAG CCC GTG GAG GCG GTG CTC         2172
Pro His Gly Phe Ala Leu Phe Ala Leu Lys Pro Val Glu Ala Val Leu
530                 535                 540

CAC CTC CCC TCC CCC GAC TGG GCC GAG GAG CCC GCC CCC GAG GAG GCC         2220
His Leu Pro Ser Pro Asp Trp Ala Glu Glu Pro Ala Pro Glu Glu Ala
545                 550                 555                 560

GAC CTG CCC CGG GTC CAC ATG CCC GGG GGG CCG GAG GTC CTC CTG GTG         2268
Asp Leu Pro Arg Val His Met Pro Gly Gly Pro Glu Val Leu Leu Val
565                 570                 575

GAC ACC CTG GTC CAC GAA AGG GGG CGG GAG GAG CTC CTA AAC GCC CTC         2316
Asp Thr Leu Vla His Glu Arg Gly Arg Glu Glu Leu Leu Asn Ala Leu
580                 585                 590

GCC CAG ACC CTG AAG GAG AAG AGC TGG CTC GCC CTC AAG CCG CAG AAG         2364
Ala Gln Thr Leu Lys Glu Lys Ser Trp Leu Ala Leu Lys Pro Gln Lys
595                 600                 605

GTG GCC CTC CTG GAC GCC CTC CGC TTC CAG AAG GAC CCG CCC CTT TAC         2412
Val Ala Leu Leu Asp Ala Leu Arg Phe Gln Lys Asp Pro Pro Lys Tyr
610                 615                 620

CTC ACC CTG CTC CAG CTG GAG AAC CAC AGG ACC CTC CAG GTC TCC CTC         2460
Leu Thr Leu Leu Gln Leu Glu Asn His Arg Thr Leu Gln Val Ser Leu
625                 630                 635                 640
```

-continued

```
CCC CTC CTC TGG TCC CCC CAG AGG CGG GAA GGC CCC GGC CTC TTC GCC       2508
Pro Leu Leu Trp Ser Pro Gln Arg Arg Glu Gly Pro Gly Leu Phe Ala
645                 650                 655

CGC ACC CAC GGC CAG CCC GGC TAC TTC TAC GAG CTC TCC TTG GAC CCA       2556
Arg Thr His Gly Gln Pro Gly Tyr Phe Tyr Glu Leu Ser Leu Asp Pro
    660                 665                 670

GGC TTC TAC CGC CTC CTC CTC GCC CGC CTT AAG GAG GGG TTT GAG GGG       2604
Gly Phe Tyr Arg Leu Leu Leu Ala Arg Leu Lys Glu Gly Phe Glu Gly
675                 680                 685

CGG AGC CTC CGG GCC TAC TAC CGC GGC CGC CAC CCG GGT CCC GTG CCC       2652
Arg Ser Leu Arg Ala Tyr Tyr Arg Gly Arg His Pro Gly Pro Val Pro
    690                 695                 700

GAG GCC GTG GAC CTC CTC CGG CCG GGA CTC GCG GCG GGG GAG GGG GTC       2700
Glu Ala Val Asp Leu Leu Arg Pro Gly Leu Ala Ala Gly Glu Gly Val
705                 710                 715                 720

TGG GTC CAG CTC GGC CTC GTC CAA GAC GGG GGC CTG GAC CGC ACG GAG       2748
Trp Val Gln Leu Gly Leu Val Gln Asp Gly Gly Leu Asp Arg Thr Glu
    725                 730                 735

CGG GTC CTC CCC CGC CTG GAC CTC CCC TGG GTT CTC CGG CCC GAA GGG       2796
Arg Val Leu Pro Arg Leu Asp Leu Pro Trp Val Leu Arg Pro Glu Gly
740                 745                 750

GGC CTC TTC TGG GAG CGG GGC GCC TCC AGA AGG GTC CTC GCC CTC ACG       2844
Gly Leu Phe Trp Glu Arg Gly Ala Ser Arg Arg Val Leu Ala Leu Thr
    755                 760                 765

GGA AGC CTC CCC CCG GGC CGC CCC CAG GAC CTC TTC GCC GCC CTG GAG       2892
Gly Ser Leu Pro Pro Gly Arg Pro Gln Asp Leu Phe Ala Ala Leu Glu
770                 775                 780

GTC CGG CTC CTG GAA AGC CTT CCC CGC CTC CGG GGG CAC GCC CCC GGG       2940
Val Arg Leu Leu Glu Ser Leu Pro Arg Leu Arg Gly His Ala Pro Gly
    785                 790                 795                 800

ACC CCA GGC CTC CTT CCC GGG GCC CTG CAC GAG ACC GAA GCC CTG GTC       2988
Thr Pro Gly Leu Leu Pro Gly Ala Leu His Glu Thr Glu Ala Leu Val
805                 810                 815

CGC CTC CTC GGG GTG CGC CTC GCC CTC CTC CAC CGG GCC CTT GGG GAG       3036
Arg Leu Leu Gly Val Arg Leu Ala Leu Leu His Arg Ala Leu Gly Glu
    820                 825                 830

GTG GAG GGG GTG GTG GGG GGC CAC CCC CTC CTA GGC CGC GGC CTC GGG       3084
Val Glu Gly Val Val Gly Gly His Pro Leu Leu Gly Arg Gly Leu Gly
835                 840                 845

GCC TTC CTG GAG CTG GAG GGG GAG GTG TAC CTC GTG GCC CTG GGC GCG       3132
Ala Phe Leu Glu Leu Glu Gly Glu Val Tyr Leu Val Ala Leu Gly Ala
    850                 855                 860

GAA AAG CGG GGC ACG GTG GAG GAG GAC CTG GCC CGC CTG GCC TAC GAC       3180
Glu Lys Arg Gly Thr Val Glu Glu Asp Leu Ala Arg Leu Ala Tyr Asp
865                 870                 875                 880

GTG GAG CGG GCC GTG CAC CTC GCC CTC GAG GCC CTG GAG GCG GAG CTT       3228
Val Glu Arg Ala Val His Leu Ala Leu Glu Ala Leu Glu Ala Glu Leu
    885                 890                 895

TGG GCC TTT GCC GAG GAG GTG GCC GAC CAC CTC CAC GCC GCC TTC CTC       3276
Trp Ala Phe Ala Glu Glu Val Ala Asp His Leu His Ala Ala Phe Leu
900                 905                 910

CAA GCC TAC CGC TCC GCC CTC CCC GAG GAG GCC CTG GAG GAG GCG GGC       3324
Gln Ala Tyr Arg Ser Ala Leu Pro Glu Glu Ala Leu Glu Glu Ala Gly
    915                 920                 925

TGG ACG CGG CAC ATG GCC GAG GTG GCG GCG GAG CAC CTC CAC CGG GAG       3372
Trp Thr Arg His Met Ala Glu Val Ala Ala Glu His Leu His Arg Glu
930                 935                 940

GAA AGG CCC GCC CGC AAG CGC ATC CAC GAG CGC TGG CAG GCC AAG GCC       3420
Glu Arg Pro Ala Arg Lys Arg Ile His Glu Arg Trp Gln Ala Lys Ala
    945                 950                 955
```

```
945              950              955              960
GGA AAA GCC                                                                3429
Gly Lys Ala
963

TAGGCGCCCG GTAGCCCTTC AGCCCCGGGC CACGGGGGCC TTGGGGTGGA AGACGGCCTC           3489

CTCGGGGAGG AGGCGGCGCT TCTTGGCCCG GCGGTAGACG GCGTCCCACA TGCGGCAGAA           3549

GGCGCACACC GCCCCCGTGG TGGGGTAGCC GCACCGCTCG CACTCCCTAA G                   3600
```

(2) INFORMATION FOR SEQ ID NO:6:

(i) SEQUENCE CHARACTERISTICS:
        (A) LENGTH:39 base pairs
        (B) TYPE:nucleic acid
        (C) STRANDEDNESS: single
        (D) TOPOLOGY:linear (ii) MOLECULE TYPE: cDNA (xi) SEQUENCE DESCRIPTION:SEQ ID NO:6:

```
AGCTTGAATT CTTTTTTAAT AAAATCAGGA GGAAAAACC                                 39
```

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
TGGTAYAARG AYGCNGT                                                        17
```

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
AAYATGTGGC CNGARGA                                                        17
```

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GTAAAACGAC GGCCAGT                                                        17
```

(2) INFORMATION FOR SEQ ID NO:10:

(i) SEQUENCE CHARACTERISTICS:
        (A) LENGTH: 46 base pairs
        (B) TYPE: nucleic acid
        (C) STRANDEDNESS: single

```
        (D) TOPOLOGY: linear (ii) MOLECULE TYPE: cDNA (xi) SEQUENCE DESCRIPTION: SEQ ID NO:10:

AGCTTGAATT CTTTTTTAAT AAAATCAGGA GGAAAAACCA TGGACC                    46

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CCCTCTGGTA CAAGGACGCG GTGATCTACC AGCTCCAC                             38

(2) INFORMATION FOR SEQ ID NO:12:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GTCCGCTCCT TCTTTGACGC CAACAACGAC GGCTACGG                             38

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GGACTTTGAG GGCCTGAGGC GGA                                             23

(2) INFORMATION FOR SEQ ID NO:14:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

AGCTTCCGCC TCAGGCCCTC AAAGTCCCCG TAGCCGTCGT TGTTG                     45

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA
```

-continued (xi) SEQUENCE DESCRIPTION: SEQ ID NO:15:

GCGTCAAAGA AGGAGCGGAC GTGGAGCTGG TAGATCACC                                       39

(2) INFORMATION FOR SEQ ID NO:16:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

GCGTCCTTGT ACCAGAGGGG GTCCATGGTT TTTCCTCC                                        38

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TGATTTTATT AAAAAAGAAT TCA                                                        23